United States Patent
Booth et al.

(10) Patent No.: US 11,062,798 B2
(45) Date of Patent: Jul. 13, 2021

(54) MANAGING INSULIN ADMINISTRATION

(71) Applicant: Aseko, Inc., Greenville, SC (US)

(72) Inventors: Robert C. Booth, Columbus, NC (US); Robert Salitsky, Greenville, SC (US); Andrew Rhinehart, Greenville, SC (US)

(73) Assignee: Aseko, Inc., Greenville, SC (US)

( * ) Notice: Subject to any disclaimer, the term of this patent is extended or adjusted under 35 U.S.C. 154(b) by 627 days.

(21) Appl. No.: 15/610,187

(22) Filed: May 31, 2017

(65) Prior Publication Data

US 2017/0351842 A1 Dec. 7, 2017

Related U.S. Application Data

(60) Provisional application No. 62/346,874, filed on Jun. 7, 2016.

(51) Int. Cl.

| | |
|---|---|
| *A61B 5/00* | (2006.01) |
| *G16H 20/17* | (2018.01) |
| *G16H 20/60* | (2018.01) |
| *G16H 40/63* | (2018.01) |
| *G16H 10/40* | (2018.01) |
| *G06F 19/00* | (2018.01) |

(52) U.S. Cl.
CPC ............ *G16H 20/17* (2018.01); *G06F 19/00* (2013.01); *G16H 10/40* (2018.01); *G16H 20/60* (2018.01); *G16H 40/63* (2018.01)

(58) Field of Classification Search
CPC .. G06F 19/00; A61B 5/04; A61B 5/00; A61B 19/00; G06G 5/00
USPC ...... 705/3; 600/300, 523, 365, 661; 128/898
See application file for complete search history.

(56) References Cited

U.S. PATENT DOCUMENTS

| | | | | |
|---|---|---|---|---|
| 5,251,126 A | * | 10/1993 | Kahn | G01N 35/00871 600/309 |
| 6,415,175 B1 | * | 7/2002 | Conley | A61N 1/37247 600/518 |
| 8,323,189 B2 | * | 12/2012 | Tran | A61B 5/0024 600/300 |

(Continued)

OTHER PUBLICATIONS

Google patents search, Jan. 10, 2020 (Year: 2020).*
Ip.com search, Mar. 9, 2021 (Year: 2021).*
Google patents search, Mar. 8, 2021 (Year: 2021).*

*Primary Examiner* — Dilek B Cobanoglu
(74) *Attorney, Agent, or Firm* — Honigman LLP; Brett A. Krueger

(57) ABSTRACT

A method includes obtaining blood glucose measurements and blood glucose times of a patient from a blood glucose meter and executing a patient management program configured to display on a screen a graphical user interface having a trend window of the blood glucose measurements on the time line. The patient management program is configured to receive, in the trend window magnifying inputs for a magnification window superimposed on a segment of the timeline to specify a date range for a magnified window. The patient management program is further configured to display the magnified window including the blood glucose measurements of the patient from the specified date range and display a first information window including quantitative information associated with the blood glucose measurements from the specified date range.

17 Claims, 20 Drawing Sheets

(56) References Cited

U.S. PATENT DOCUMENTS

| | | | |
|---|---|---|---|
| 8,597,570 B2* | 12/2013 | Terashima | A61B 5/721 |
| | | | 422/68.1 |
| 8,830,272 B2* | 9/2014 | Samra | G06F 17/241 |
| | | | 345/661 |
| 9,092,553 B2* | 7/2015 | Weinert | A61B 5/14532 |
| 9,465,910 B2* | 10/2016 | Minor | G16B 99/00 |
| 2006/0272652 A1* | 12/2006 | Stocker | G16H 50/50 |
| | | | 128/898 |
| 2011/0053121 A1* | 3/2011 | Heaton | A61B 5/14532 |
| | | | 434/127 |
| 2011/0196213 A1* | 8/2011 | Thukral | A61B 5/7275 |
| | | | 600/301 |
| 2014/0324469 A1* | 10/2014 | Reiner | G16H 50/20 |
| | | | 705/3 |
| 2015/0289823 A1* | 10/2015 | Rack-Gomer | G16H 40/63 |
| | | | 600/365 |

* cited by examiner

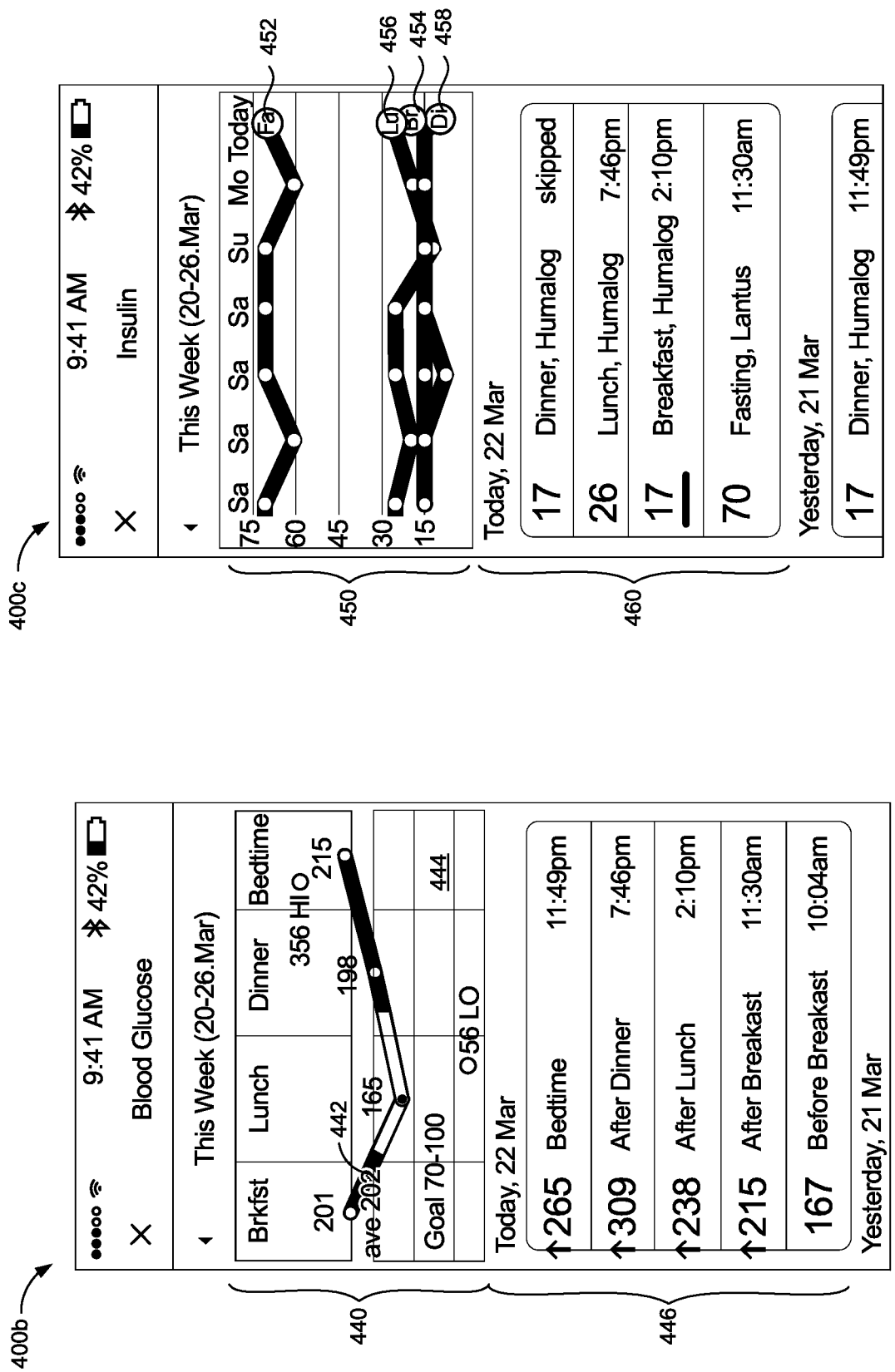

Building Insulin Dosage

MANAGING INSULIN ADMINISTRATION

CROSS REFERENCE TO RELATED APPLICATIONS

This U.S. patent application claims priority under 35 U.S.C. § 119(e) to U.S. Provisional Application 62/346,874, filed on Jun. 7, 2016, which is hereby incorporated by reference in its entirety.

TECHNICAL FIELD

This disclosure relates to a system for managing insulin administration or insulin dosing.

BACKGROUND

Managing diabetes requires calculating insulin doses for maintaining blood glucose measurements within desired ranges. Managing diabetes requires calculating insulin doses for maintaining blood glucose measurements within desired ranges. Manual calculation may not be accurate due to human error, which can lead to patient safety issues. Different institutions use multiple and sometimes conflicting protocols to manually calculate an insulin dosage. Moreover, the diabetic population includes many young children or elderly persons whom have difficulty understanding calculations for insulin doses.

SUMMARY

One aspect of the disclosure provides a method for managing insulin administration or insulin dosing. The method includes obtaining, at data processing hardware, blood glucose measurements of a patient and blood glucose times associated with a time of measuring each blood glucose measurement from a blood glucose meter associated with the patient, and executing, at the data processing hardware, a patient management program configured to display on a screen in communication with the data processing hardware a graphical user interface having a trend window of the blood glucose measurements on a timeline. The patient management program is configured to receive, in the trend window, magnifying inputs from a medical professional for a magnification window superimposed on a segment of the timeline to specify a date range for a magnified window and display, in the graphical user interface, the magnified window including the blood glucose measurements of the patient from the specified date range. The blood glucose measurements of the magnified window include interactive points within associated ones of scheduled blood glucose time intervals based on the blood glucose times. The patient management program is also configured to display, in the graphical user interface, a first information window including quantitative information associated with the blood glucose measurements from the specified date range.

Implementations of the disclosure may include one or more of the following optional features. In some implementations, the patient management program is configured to superimpose, in the graphical user interface, a first line on the magnified window representing an upper blood glucose limit of a target blood glucose range and superimpose, in the graphical user interface, a second line on the magnified window representing a lower blood glucose limit of the target blood glucose range. The interactive points associated with the blood glucose measurements within the target blood glucose range may display as a first representation, the interactive points associated with the blood glucose measurements greater than the upper blood glucose limit display as a second representation, and the interactive points associated with the blood glucose measurements less than the lower blood glucose limit display as a third representation or the second representation.

In some examples, the patient management program is configured to, in response to receiving the magnifying inputs, determine a representative average blood glucose value for each of the scheduled blood glucose time intervals and superimpose, in the graphical user interface, an average blood glucose graphic on the magnified window based on the representative average blood glucose values for the scheduled blood glucose time intervals. The patient management program may also be configured to receive, in the magnified window; filtering inputs from the medical professional to define a specified time range for the magnified window, query memory hardware in communication with the data processing hardware to obtain quantitative information related to the blood glucose measurements within the specified time range of the magnified window, and display, in the graphical user interface, a second information window including the quantitative information related to the blood glucose measurements within the specified time range of the magnified window. The interactive points associated with the blood glucose measurements within the specified time range of the magnified window may display as a first representation and the blood glucose measurements outside the specified time range of the magnified window display as a second representation different from the first representation.

In some implementations, the patient management program may receive the filtering inputs from the medical professional when the medial professional manipulates a first interactive cursor superimposed on the magnified window to set a lower time limit for the specified time range of the magnified window and/or manipulates a second graphical cursor superimposed on the magnified window to set an upper time limit for the specified time range of the magnified window. The patient management program may also be configured to, in response to the medical professional selecting one of the interactive points on the magnified window: illuminate the selected interactive point of the magnified window; query memory hardware in communication with the data processing hardware to obtain quantitative information related to the blood glucose measurement associated with the selected interactive point; and display a pop-up window including the quantitative information related to the blood glucose measurement associated with the selected interactive point.

The quantitative information may include at least one of an average blood glucose value, an aggregated blood glucose value for each of the scheduled blood glucose time intervals, a hemoglobin A1c value, an average number of blood glucose measurements per day, an average total daily dose of insulin, or average doses of insulin injected by the patient during each of the scheduled blood glucose time intervals. Obtaining the blood glucose measurements of the patient may include receiving, at the data processing hardware, the blood glucose measurements of the patient and the blood glucose times from a patient device in communication with the data processing hardware and the blood glucose meter.

Another aspect of the disclosure provides a second method for managing insulin administration or insulin dosing. The method includes obtaining, at data processing hardware; blood glucose measurements of a patient and blood glucose times associated with a time of measuring each blood glucose measurement from a blood glucose meter associated with the patient and executing, at the data processing hardware, a patient management program configured to display on a screen in communication with the data processing hardware a graphical user interface having a trend window of the blood glucose measurements on a timeline. The patient management program is configured to receive, in the trend window, magnifying inputs from a medical professional for a magnification window superimposed on a segment of the timeline to specify a date range for a magnified window and display, in the graphical user interface, the magnified window including the blood glucose measurements of the patient from the specified date range. The blood glucose measurements of the magnified window includes a blood glucose plot extending through each date of the specified date range. The patient management program is also configured to display, in the graphical user interface, a first information window including quantitative information associated with the blood glucose measurements from the specified date range.

This aspect may include one or more of the following optional features. In some implementations, the patient management program is configured to, in response to receiving the magnifying inputs determine an estimated hemoglobin A1c value for each date of the specified date range and superimpose, in the graphical user interface, an average hemoglobin A1c graphic on the magnified window based on the estimated hemoglobin A1c values of the specified date range. The patient management program may also be configured to, in response to receiving the magnifying inputs: determine a daily average blood glucose value for each date of the specified date range; and superimpose, in the graphical user interface, an average blood glucose graphic on the magnified window based on the daily average blood glucose values for the specified date range.

In some examples, the patient management program is configured to: in response to receiving the magnifying inputs: query memory hardware in communication with the data processing hardware to obtain doses of insulin administered by the patient for each date of the specified date range; and superimpose, in the graphical user interface, a plot of the doses of insulin administered by the patient for each date of the specified date range on the magnified window. The patient management program may also be configured to display, in the graphical user interface, a communication window including a history of communications with the patient. The patient management program may further be configured to display, in the graphical user interface, a monitoring window including a list of patients under the supervision of the medical professional. In some implementations, the patient management program is configured to: determine an alert condition for one of the patients when a most recent blood glucose measurement of the patient is less than a hypoglycemia blood glucose threshold or greater than a hyperglycemia blood glucose threshold; and superimpose, in the graphical user interface, an alert graphic on the monitoring window proximate to the patient associated with the alert condition. The alert graphic includes a value of the most recent blood glucose measurement associated with the alert condition.

Yet another aspect of the disclosure provides a third method for managing insulin administration or insulin dosing. The method includes receiving, at data processing hardware, a current blood glucose measurement of a patient from a patient device. The patient device executes an insulin management program configured to: display, on a patient screen of the patient device, a blood glucose input field; receive, at the blood glucose input field, the current blood glucose measurement; and transmit the current blood glucose measurement and a blood glucose time associated with a time of measuring the current blood glucose measurement to the data processing hardware. In response to receiving the current blood glucose measurement, the method includes obtaining, by the data processing hardware, blood glucose parameters associated with the patient from memory hardware in communication with the data processing hardware. The blood glucose parameters include a hypoglycemia blood glucose value, a target blood glucose value greater than the hypoglycemia blood glucose value, and a correction factor. The method also includes comparing, by the data processing hardware, the current blood glucose measurement to the blood glucose parameters. When the current blood glucose measurement is less than the hypoglycemia blood glucose value, the method includes transmitting a low blood glucose alert notification from the data processing hardware to the patient device. The low blood glucose alert notification, when received by the patient device, causes the insulin management program to render a hypoglycemia view on the patient screen. The hypoglycemia view displays: hypoglycemia patient instructions to treat a hypoglycemia episode associated with the current blood glucose measurement; a countdown timer indicating a remaining amount of time until the patient is instructed to attain a subsequent blood glucose measurement; and one or more patient-selectable hypoglycemia buttons each indicating respective ones of potential causes for the hypoglycemia episode.

This aspect may include one or more of the following optional features. In some implementations, prior to receiving the current blood glucose measurement, the method includes determining, by the data processing hardware, whether a current time is within a scheduled blood glucose time interval requiring the current blood glucose measurement. When the current time is within the scheduled blood glucose time interval requiring the current blood glucose measurement, the method may include transmitting a blood glucose request notification from the data processing hardware to the patient device during the scheduled blood glucose time interval. The blood glucose request notification, when received by the patient device, may cause the insulin management program to display the blood glucose request notification on the patient screen. The blood glucose request notification may instruct the patient to attain the current blood glucose measurement. The blood glucose request notification may include an interactive graphic or user-selectable link and the insulin management program may be configured to display the blood glucose input field on the patient screen in response to the patient selecting the blood glucose request notification.

In some examples, the insulin management program executing on the patient device is configured to display a patient-selectable meal type button on the patient screen indicating a meal type when the patient is consuming a meal based on the blood glucose time. Selecting the meal type button by the patient may cause the insulin management program to prompt the patient to input a meal size for the meal type and transmit the input meal size to the data processing hardware. The patient device may also be configured to display a patient-selectable non-meal button on the patient screen indicating that the current blood glucose measurement is dissociated from the meal type indicated by the patient-selectable meal type button. Selecting the non-meal button by the patient may cause the insulin management program to prompt the patient to input a rational for obtaining the current blood glucose measurement and transmit the input rational to the data processing hardware. The insulin management program may display the blood glucose input field, the patient-selectable meal type button, and the patient-selectable non-meal button in a common view on the patient screen. The meal type may include at least one of a pre-breakfast blood glucose measurement, a pre-lunch blood glucose measurement, a pre-dinner blood glucose measurement, or a bedtime blood glucose measurement. The pre-breakfast, pre-lunch, pre-dinner, and bedtime blood glucose measurements may be scheduled in a daily repetitive rotational order.

When the current blood glucose measurement is greater than the target blood glucose value, the method may include determining, by the data processing hardware, a correction dose for the patient based on a function of the current blood glucose measurement, the target blood glucose value, and the correction factor. The method may also include transmitting the correction dose for the patient from the data processing hardware to the patient device. The correction dose when received by the patient device, may cause the insulin management program to display a value of the correction dose on the patient screen.

After receiving the current blood glucose measurement of the patient, the method may include obtaining, by the data processing hardware, a meal type for the patient based on the blood glucose time associated with the time of measuring the current blood glucose measurement and receiving a meal size for the meal type at the data processing hardware from the patient device. The patient device may receive the meal size at a meal size input displayed by the insulin management program on the patient screen. The method may also include determining, by the data processing hardware, a recommended meal bolus for the patient based on the meal size and the meal type and transmitting the recommended meal bolus from the data processing hardware to the patient device. The recommended meal bolus, when received by the patient device; may cause the insulin management program to display on the patient screen: a value of the recommended meal bolus; a recommended total dosage of insulin for the patient based on a sum of the values of the recommended meal bolus and the correction dose; and a patient-selectable change dosage button enabling the patient to change the recommended total dosage of insulin when the patient selects the patient-selectable change dosage button.

In some examples, the patient inputs the meal size to the patient device by selecting one of multiple meal size buttons displayed on the patient screen, each meal size button corresponding to a respective meal size associated with the meal type. The patient may input the meal size to the patient device by inputting a number of carb exchanges associated with the meal type. The patient may input the meal size to the patient device by inputting an amount of carbohydrates associated with the meal type.

The details of one or more implementations of the disclosure are set forth in the accompanying drawings and the description below. Other aspects, features, and advantages will be apparent from the description and drawings, and from the claims.

DESCRIPTION OF DRAWINGS

FIGS. 4A-4C are schematic views of example graphical user interfaces displaying blood glucose data for a patient.

FIGS. 6A-6C are schematic views of example graphical user interfaces for logging blood glucose measurements.

FIGS. 7A-7D are schematic views of example graphical user interfaces for determining a meal bolus for a patient.

FIGS. 9A and 9B are schematic views of example graphical user interfaces prompting a patient to provide a rational for obtaining a blood glucose measurement not associated with a scheduled meal type.

Like reference symbols in the various drawings indicate like elements.

DETAILED DESCRIPTION

Persons with diabetes must manage their blood glucose level within desired ranges, typically by using multiple daily injections (MDI) therapy that includes injection doses of long-acting (basal) insulin; bolus insulin at meals and correction bolus injections during other periods of hyperglycemia. Insulin doses must be individualized for each patient. Too much insulin can cause hypoglycemia, coma, and death; too little insulin can cause hyperglycemia and other complications. Providers often use a variety of methods to adjust a patient's insulin dose: some may use formulas of their own; some may use paper protocols that are complex and difficult for the patients to follow, leading to a high incidence of human error; and some may use heuristic methods. Moreover, patients must periodically make clinical visits to adjust their treatment plan based on historical blood glucose information since their last visit. Therefore, it is desirable to have a clinical support system 100 (FIG. 1) that remotely monitors a patient's blood glucose level and enables healthcare providers to communicate treatment plans, or modifications thereto, to their patients on a day-by-day basis.

Figure 1:
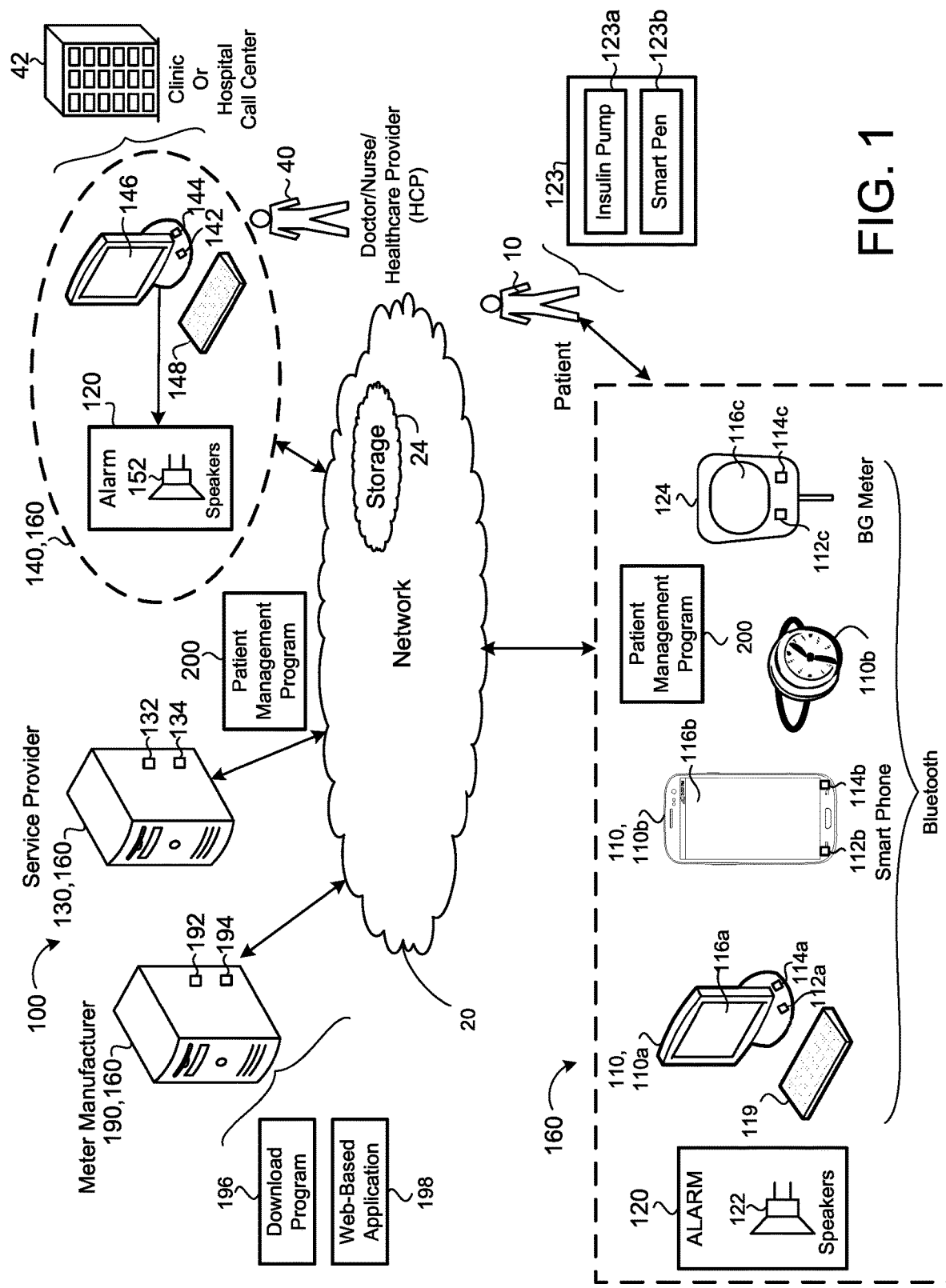
FIG. 1 is a schematic view of an exemplary system for monitoring blood glucose levels of a patient.

Referring to FIG. 1, in some implementations, a clinical decision support system 100 analyzes inputted patient condition parameters for one or more patients 10 and calculates a personalized dose of insulin to bring and maintain each patient's blood glucose level into a target blood glucose range $BG_{TR}$. As used herein; the patient 10 refers to an outpatient that may be located at some remote location, such as the patient's 10 residence or place of employment. As used herein, the term "clinical" may refer to a hospital call center. The system 100 may monitor the glucose levels of a patient 10 and calculate a recommended subcutaneous insulin dose to bring the patient's blood glucose into the preferred target range $BG_{TR}$ over a recommended period of time. Moreover, the system 100 provides notifications to the patient 10 that include hypoglycemia patient instructions to bring the patient's blood glucose into the target range $BG_{TR}$ when the patient's blood glucose is below a hypoglycemia blood glucose value and blood glucose request notifications requesting the patient 10 to attain a blood glucose measurement during a scheduled blood glucose time interval as indicated by the patient condition parameters input to the system 10. A qualified and trained healthcare professional (HCP) 40 may use the system 100 along with clinical reasoning to determine the proper dosing administered to a patient 10. Therefore, the system 100 is a glycemic management tool for evaluation of a patient's current and cumulative blood glucose value BG while taking into consideration the patient's information such as age, weight, and height. The system 100 may also consider other information such as carbohydrate content of meals, insulin doses being administered to the patient 10, e.g., long-acting insulin doses for basal insulin and rapid-acting insulin doses for meal boluses and correction boluses. Based on those measurements (that may be stored in non-transitory memory 24, 114, 144), the system 100 recommends a subcutaneous basal and bolus insulin dosing recommendation or prescribed dose to adjust and maintain the blood glucose level towards a configurable (based on the patient's information) physician's determined blood glucose target range $BG_{TR}$. The system 100 also considers a patient's insulin sensitivity or unproved glycemic management and outcomes. The system 100 may take into account pertinent patient information such as demographics and previous results, leading to a more efficient use of healthcare resources. Finally, the system 100 provides a reporting platform for reporting the recommendations or prescribed dose(s) to the user 40 and the patient 10. In addition, the system 100 provides faster, more reliable, and more efficient insulin administration than a human monitoring the insulin administration. The system 100 reduces the probability of human error and insures consistent treatment, due to the system's capability of storing and tracking the patient's blood glucose levels BG, which may be used for statistical studies. The system 100 provides a meal-by-meal adjustment of Meal Boluses without carbohydrate counting, by providing a dedicated subprogram that adjusts meal boluses based on the immediately preceding meal bolus and the BG that followed it. The system 100 provides a meal-by-meal adjustment of Meal Boluses with carbohydrate counting by providing a dedicated subprogram that adjusts meal boluses based a Carbohydrate-to-Insulin Ratio (CIR) that is adjusted at each meal, based on the CIR used at the immediately preceding meal bolus and the BG that followed it.

The system 100 may also enable the HCP 40, or multiple HCPs, to view blood glucose measurements and doses of insulin for one or more patients 10. For instance, the HCP may view a trend window of blood glucose measurements on a timeline and interactively specify date ranges over the timeline to view at least the blood glucose measurements for a given patient 10 during the specified date ranges. Additionally, the system 100 may alert the HCP 40 when a patient 10 under the HCP's 40 care has a low blood glucose measurement or has not entered his/her blood glucose measurement during a scheduled blood glucose time interval as indicated by the patient condition parameters input to the system 100. For example, the system 100 may alert the HCP 40 when a lunchtime blood glucose measurement has not been received from one of the patients. Thereafter, the HCP 40 may send a blood glucose request notification requesting the patient 10 to attain the lunchtime blood glucose measurement. Alternatively, the system 100 may automatically send the blood glucose request notification when the lunchtime blood glucose measurement has not been received.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's blood glucose level is below a preferred target. Appropriate management of blood glucose levels for critically ill patients reduces co-morbidities and is associated with a decrease in infection rates, length of hospital stay, and death. The treatment of hyperglycemia may differ depending on whether or not a patient has been diagnosed with Type 1 diabetes mellitus, Type 2 diabetes mellitus, gestational diabetes mellitus, or non-diabetic stress hyperglycemia. The blood glucose target range $BG_{TR}$ is defined by a lower limit, i.e., a low target $BG_{TRL}$ and an upper limit, i.e., a high target $BG_{TRH}$.

Diabetes Mellitus has been treated for many years with insulin. Some recurring terms and phrases are described below:

Injection: Administering insulin by means of manual syringe or an insulin "pen," with a portable syringe named for its resemblance to the familiar writing implement.

Infusion: Administering insulin in a continuous manner by means of an insulin pump for subcutaneous insulin apparatus 123a capable of continuous administration.

Basal-Bolus Therapy: Basal-bolus therapy is a term that collectively refers to any insulin regimen involving basal insulin and boluses of insulin.

Basal Insulin: Insulin that is intended to metabolize the glucose released by a patient's the liver during a fasting state. Basal insulin is administered in such a way that it maintains a background level of insulin in the patient's blood, which is generally steady but may be varied in a programmed manner by an insulin pump 123a. Basal insulin is a slow, relatively continuous supply of insulin throughout the day and night that provides the low, but present, insulin concentration necessary to balance glucose consumption (glucose uptake and oxidation) and glucose production (glucogenolysis and gluconeogenesis). A patient's Basal insulin needs are usually about 10 to 15 mU/kg/hr and account for 30% to 50% of the total daily insulin needs; however, considerable variation occurs based on the patient 10.

Bolus Insulin: Insulin that is administered in discrete doses. There are two main types of boluses, Meal Bolus and Correction Bolus.

Meal Bolus: Taken just before a meal in an amount which is proportional to the anticipated immediate effect of carbohydrates in the meal entering the blood directly from the digestive system. The amounts of the Meal Boluses may be determined and prescribed by a physician 40 for each meal during the day, i.e., breakfast, lunch, and dinner. Alternatively, the Meal Bolus may be calculated in an amount generally proportional to the number of grams of carbohydrates in the meal. The amount of the Meal Bolus is calculated using a proportionality constant; which is a personalized number called the Carbohydrate-to-Insulin Ratio (CIR) and calculated as follows:

$$\text{Meal Insulin Bolus} = \{\text{grams of carbohydrates in the meal}\}/\text{CIR} \qquad (1)$$

Correction Bolus CB: Injected immediately after a blood glucose measurement; the amount of the correction bolus is proportional to the error in the BG (i.e., the bolus is proportional to the difference between the blood glucose measurement BG and the patient's personalized Target blood glucose $BG_{Target}$). The proportionality constant is a personalized number called the Correction Factor, CF. The Correction Bolus is calculated as follows:

$$CB=(BG-BG_{Target})/CF \quad (2)$$

A Correction Bolus CB is generally administered in a fasting state, after the previously consumed meal has been digested. This often coincides with the time just before the next meal.

In some implementations, blood glucose measurements BG are aggregated using an exponentially-weighted moving average $EMA_t$ as a function for each modal day's time interval BG. The $EMA_t$ is calculated as follows:

$$EMA_t=\alpha(BG_t)+(1-\alpha)EMA_{t-1}, \quad (3)$$

wherein:

$$\alpha=2/(n+1),$$

wherein n is the number of equivalent days averaged. In other embodiments, an arithmetic moving average is utilized that calculates the sum of all BG values in n days divided by a total count (n) of all values associated with the arithmetic average.

There are several kinds of Basal-Bolus insulin therapy including Insulin Pump therapy and Multiple Dose Injection therapy:

insulin Pump Therapy: An insulin pump 123a is a medical device used for the administration of insulin in the treatment of diabetes mellitus, also known as continuous subcutaneous insulin infusion therapy. The device includes: a pump, a disposable reservoir for insulin, and a disposable infusion set. The pump 123a is an alternative to multiple daily injections of insulin by insulin syringe or an insulin pen and allows for intensive insulin therapy when used in conjunction with blood glucose monitoring and carbohydrate counting. The insulin pump 123a is a battery-powered device about the size of a pager. It contains a cartridge of insulin, and it pumps the insulin into the patient via an "infusion set", which is a small plastic needle or "canula" fitted with an adhesive patch. Only rapid-acting insulin is used.

Multiple Dose Injection (MDI): MDI involves the subcutaneous manual injection of insulin several times per day using syringes or insulin pens 123b. Meal insulin is supplied by injection of rapid-acting insulin before each meal in an amount proportional to the meal. Basal insulin is provided as a once, twice, or three time daily injection of a dose of long-acting insulin. Other dosage frequencies may be available. Advances continue to be made in developing different types of insulin, many of which are used to great advantage with MDI regimens:

Long-acting insulins are non-peaking and can be injected as infrequently as once per day. These insulins are widely used for Basal Insulin. They are administered in dosages that make them appropriate for the fasting state of the patient, in which the blood glucose is replenished by the liver to maintain a steady minimum blood glucose level.

Rapid-acting insulins act on a time scale shorter than natural insulin. They are appropriate for boluses.

The system 100 is configured to facilitate real-time communication between the patient 10 and the HCP 40 by evaluating a blood glucose level and nutritional intake of the patient 10 to provide the patient 10 with a recommended treatment plan for maintaining the patient's blood glucose level within the blood glucose target range $BG_{TR}$. For instance, based on the evaluation and analysis of the data, the system 100 calculates an insulin dose, which is administered to the patient 10 to bring and maintain the blood glucose level of the patient 10 into the blood glucose target range $BG_{TR}$. The system 100 may be applied to various devices, including, but not limited to, subcutaneous insulin infusion pumps 123a, insulin pens 123b, glucometers 124, continuous glucose monitoring systems, and glucose sensors.

In some examples the clinical decision support system 100 includes a network 20, a patient device 110, a dosing controller 160, a service provider 130, an HCP medical record system 140, and a meter manufacturer provider 190. The patient device 110 may include, but is not limited to, desktop computers 110a or portable electronic device 110b (e.g., cellular phone, smartphone, smartwatch, personal digital assistant, barcode reader, personal computer, or a wireless pad) or any other electronic device capable of sending and receiving information via the network 20. In some implementations, one or more of the patient's glucometer 124, insulin pump 123a, or insulin pen 123b are capable of sending and receiving information via the network 20.

The patient device 110a, 110b, includes data processing hardware 112a, 112b (e.g., a computing device that executes instructions), and non-transitory memory 114a, 114b and a display 116a, 116b (e.g., touch display or non-touch display) in communication with the data processor 112. The data processing hardware 112 may execute a patient management program 200 that allows the patient 10 to input blood glucose measurements to the patient device 110 and transmit the blood glucose measurement over the network 20 to at least one of the dosing controller 160, the service provider 130, the health care provider medical record system 140, or the meter manufacturer provider 190. In some implementations, the patient management program 200 is configured to graphically display (e.g., via a graphical user interface (GUI) on the display 116a, 116) a recommended treatment on the patient device 110 for managing the patient's blood glucose level. In some examples, the patient device 110 includes a keyboard 119, speakers 122, microphones, mouse, and a camera.

The glucometer 124, insulin pump 123a, and insulin pen 123b associated with the patient 10 include a data processor 112c (e.g., a computing device that executes instructions), and non-transitory memory 114c and a display 116c (e.g., touch display or non-touch display in communication with the data processor 112c.

The meter manufacturer provider 190 may include may include a data processor 192 in communication with non-transitory memory 194. The data processor 192 may execute a proprietary download program 196 for downloading blood glucose BG data from the memory 114c of the patient's glucometer 124. In some implementations, the proprietary download program 196 is associated with the patient management program 200 and implemented on the HCP's 140 computing device 142 or the patient's 10 device 110a for downloading the BG data from memory 114c. In some examples, the download program 196 exports a BG data file for storage in the non-transitory memory 24, 114, 144. The data processor 192 may further execute a web-based application 198 for receiving and formatting BG data transmitted from one or more of the patient's devices 110a, 110b, 124, 123a, 123b and storing the BG data in non-transitory memory 24, 114, 144.

The service provider 130 may include a data processor 132 in communication with non-transitory memory 134. The service provider 130 provides the patient 10 and/or the HCP 40 with the patient management program 200 (e.g., a mobile application, a web-site application, or a downloadable program that includes a set of instructions) executable on a processor 112, 132, 142 of the dosing controller 160 and accessible through the network 20 via the patient device 110 and/or the health care provider electronic medical record systems 140. In some examples, the patient management program 200 is accessible through the network 20 via the portable blood glucose measurement devices 124 (e.g., glucose meter or glucometer) or portable administration devices 123a, 123b.

Figure 2:
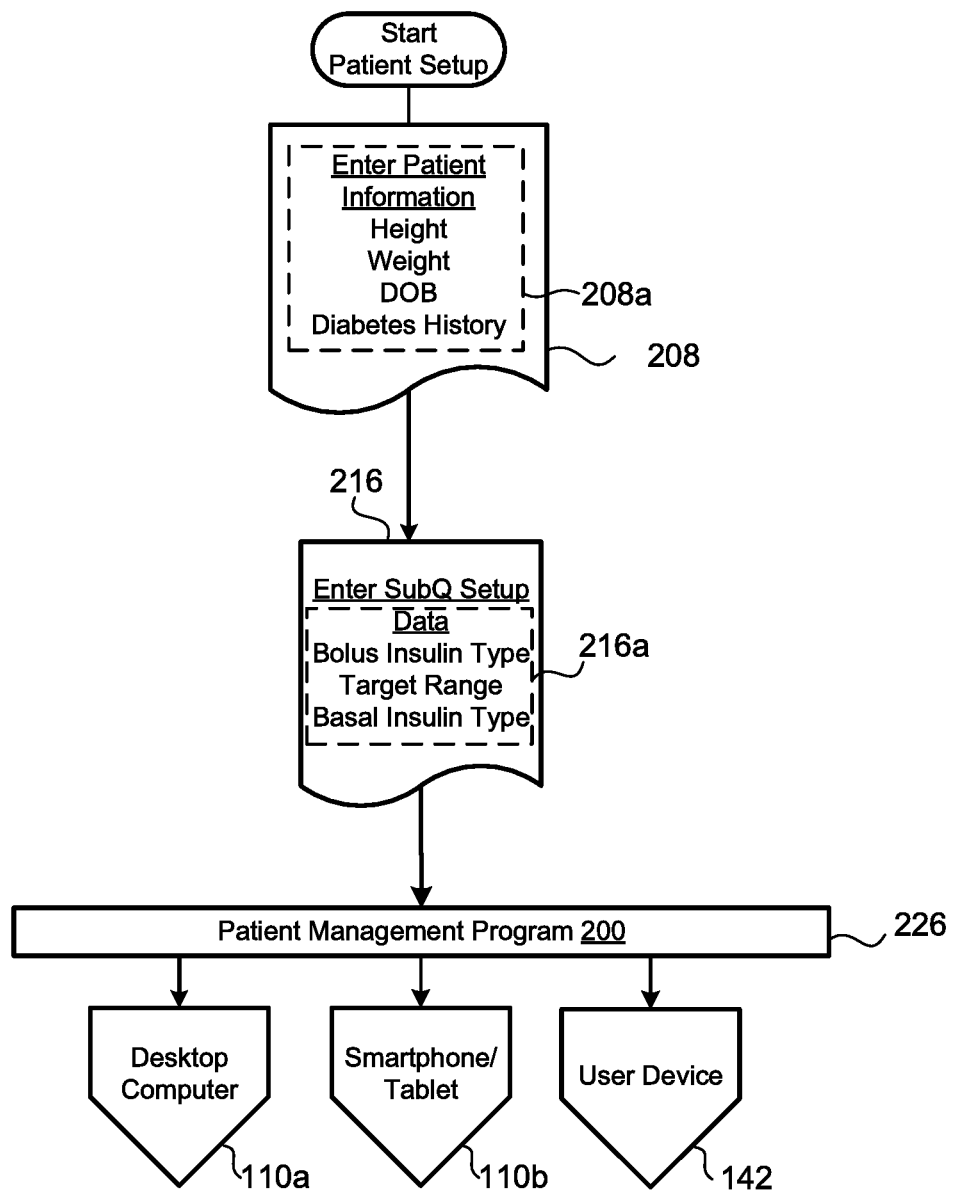
FIG. 2 is a schematic view of an exemplary program for managing the blood glucose level of a patient.

In some implementations, the HCP medical record system 140 is located at a doctor's office, clinic 42, or a facility administered by a hospital (such as a hospital call center)) and includes data processing hardware 142, a non-transitory memory 144, and a display 146 (e.g., touch display or non-touch display). The non-transitory memory 144 and the display 146 are in communication with the data processing hardware 142. The data processing hardware 142 may execute the patient management program 200 for allowing the HCP 40 to graphically view the patient's blood glucose measurements on the display 146 and provide a recommended treatment to the patient 10. In some examples, the HCP electronic medical system 140 includes a keyboard 148 in communication with the data processor 142 to allow a user (e.g., the HCP 40) to input data, such as patient information 208a (FIG. 2). The non-transitory memory 144 maintains patient records capable of being retrieved, viewed, and, in some examples, modified and updated by authorized hospital personal using the patient management program 200 and displaying on the display 146.

The dosing controller 160 is in communication with the glucometer 124, insulin administration device 123a, 123b and includes a computing device 112, 132, 142 and non-transitory memory 114, 134, 144 in communication with the computing device 112, 132, 142. The dosing controller 160 executes the patient management program 200. The dosing controller 160 stores patient related information obtained from the patient device 110, the glucometer 124, and or the HCP medical record system 140 to determine insulin doses and dosing parameters based on the received blood glucose measurement BG.

As used herein, the patient management program 200 may refer to computer software that causes a computing device 112, 132 to perform a task. In some examples, the patient management program 200 may be referred to as an "application," an "app," or a "program." Programs can be executed on a variety of computing devices, including mobile computing devices such as smart phones, tablets, and wearable computing devices (e.g., headsets and/or watches). Programs can also be executed on other types of computing devices having other form factors, such as laptop computers, desktop computers, or other consumer electronic devices. In some examples, programs may be installed on a computing device prior to a user/patient purchasing the device. In other examples, the patient/user may download and install applications on the computing device after purchasing the device.

The administration device 123 may include the insulin pump 123a or the pen 123b. The administration device 123 is in communication with the glucometer 124 and includes a computing device 112 and non-transitory memory 114 in communication with the computing device 112. The administration device 123 includes a doser in communication with the administration computing device 112 for administering insulin to the patient. For instance, the insulin pump 123a includes an infusion set including a tube in fluid communication with an insulin reservoir and a cannula inserted into the patient's 10 body and secured via an adhesive patch. The pen 123b includes a needle for insertion into the patients 10 for administering insulin from an insulin cartridge. The administration device 123 may receive and execute subcutaneous insulin treatment program selected by and transmitted from the dosing controller 160. The administration devices 123a, 123b may be "smart" administration devices capable of communicating with the dosing controller 160 to populate recommended doses of insulin for administering to the patient 10. For instance, units for the doses of insulin may be automatically set or dialed in by the administration device 123a, 123b and administered to the patient 10.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

The patient management program 200 implement an alarm system 120 that alerts a user 40 at the clinic 42 (or hospital call center) when the patient's blood glucose level BG is outside the target range $BG_{TR}$. The alarm system 120 may produce an audible sound via speaker 122 in the form of a beep or some like audio sounding mechanism. For instance, the alarm system 120 may produce an audible sound via a speaker 122 of the mobile device 110b. In some examples, the alarm system 120 displays a warning message or other type of indication on the display 116 of the patient device 110 to provide a warning message. The alarm system 120 may also send the audible and/or visual notification via the network 20 to the clinic system 140 (or any other remote station) for display on the display 146 of the clinic system 140 or played through speakers 152 of the clinic system 140.

Referring to FIG. 2, the program 200 receives parameters (e.g., patient condition parameters) inputted via the client device 110, the service provider 130, and/or the clinic system 140, analyzes the inputted parameters, and determines a personalized dose of insulin to bring and maintain a patient's blood glucose level BG into a preferred target range $BG_{TR}$ for the patient management program 200. The patient management program may refer to a subcutaneous (SubQ) outpatient program 200 or insulin treatment program 200 for treating a diabetic outpatient 10 remotely by sending/receiving communications through the network 20.

The program 200 prompts a user 40 to input patient information 208a at block 208. The user 40 may input the patient information 208a, for example, via the user device 140 or via the health care provider medical record systems 140 located at a clinic 42 (or a doctor's office or HCP). The user 40 may input new patient information 208a and the program 200 may retrieve the patient information 208a from the non-transitory memory 144 of the clinic's electronic medical system 140 or the non-transitory memory 114 of the patient device 110 (e.g., where the patient information 208a was previously entered and stored). The patient information 208a may include, but is not limited to, a patient's name, a patient's identification number (ID), a patient's height, weight, date of birth, diabetes history, physician name, emergency contact, hospital unit, diagnosis, gender, room number, and any other relevant information.

The program 200 flows to block 216, where the user 40 enters patient subcutaneous information 216a (e.g., blood glucose parameters), such as bolus insulin type, target range, target BG value, hypoglycemia BG value, hyperglycemia BG value, correction factor (CF), basal insulin type and frequency of distribution (e.g., 1 dose per day, 2 doses per day, 3 doses per day, etc.), patient diabetes status, subcutaneous type ordered for the patient (e.g., Basal/Bolus and correction) that is intended for patients on a consistent carbohydrate diet, frequency of patient blood glucose measurements, or any other relevant information. In some implementations, the patient subcutaneous information 216a is prepopulated with default parameters, which may be adjusted or modified. When the user 40 enters the patient subcutaneous information 216a, the user selects the program 200 to execute at block 226. The patient subcutaneous information 216a may further include a total daily dosage (TDD) calculated following a period on Intravenous Insulin in accordance with equation:

$$TDD = QuickTransitionConstant * M_{Trans} \quad (4A)$$

where QuickTransitionConstant is usually equal to 1000, and $M_{Trans}$ is the patient's multiplier at the time of initiation of the SubQ transition process. In other implementations, the TDD is calculated by a statistical correlation of TDD as a function of body weight. The following equation is the correlation used:

$$TDD = 0.5 * Weight\ (kg) \quad (4B)$$

In other implementations, the patient's total daily dose TDD is calculated in accordance with the following equation:

$$TDD = (BG_{Target} - K) * (M_{Trans}) * 24 \quad (4C)$$

where $M_{Trans}$ is the patient's multiplier at the time of initiation of the SubQ transition process.

In some implementations, the user 40 selects to initiate the patient management program 200 executing on the dosing controller 160 to provide recommended insulin dosing (bolus/basal) for a patient 10 to a patient device 110 associated with the patient 10. The user 40 may configure the patient management program 200 by selecting the patient device 110 used by the patient 10. Selection of block 110a indicates information for the patient's desktop computer 110a, including communication capabilities with other devices and/or the network 20. Selection of block 110b indicates information for the patient's 10 smartphone 110b, tablet or smart watch, including communication capabilities with the glucometer 124 and/or the insulin administration devices 123a, 123b, As used herein, a smartwatch or tablet can similarly be used to implement the same functionality as the smartphone 110b described herein. For instance, the smartphone 110b may communicate with the glucometer 124 via Bluetooth or other connection to download BG data from the memory 114c of the glucometer, and transmit the downloaded BG data through the network 20. In other examples, the smartphone 110b may receive recommended insulin doses over the network 20 from the dosing controller 160 and provide the recommended insulin doses to the glucometer 124 and/or insulin administration device 123a, 123b. The user 40 may also select to execute the patient management program 200 on the user device 142 to receive blood glucose measurements and/or administered doses of inulin from the patient device. For instance, selection of block 142 indicates information for the user device 142.

Figure 3A:
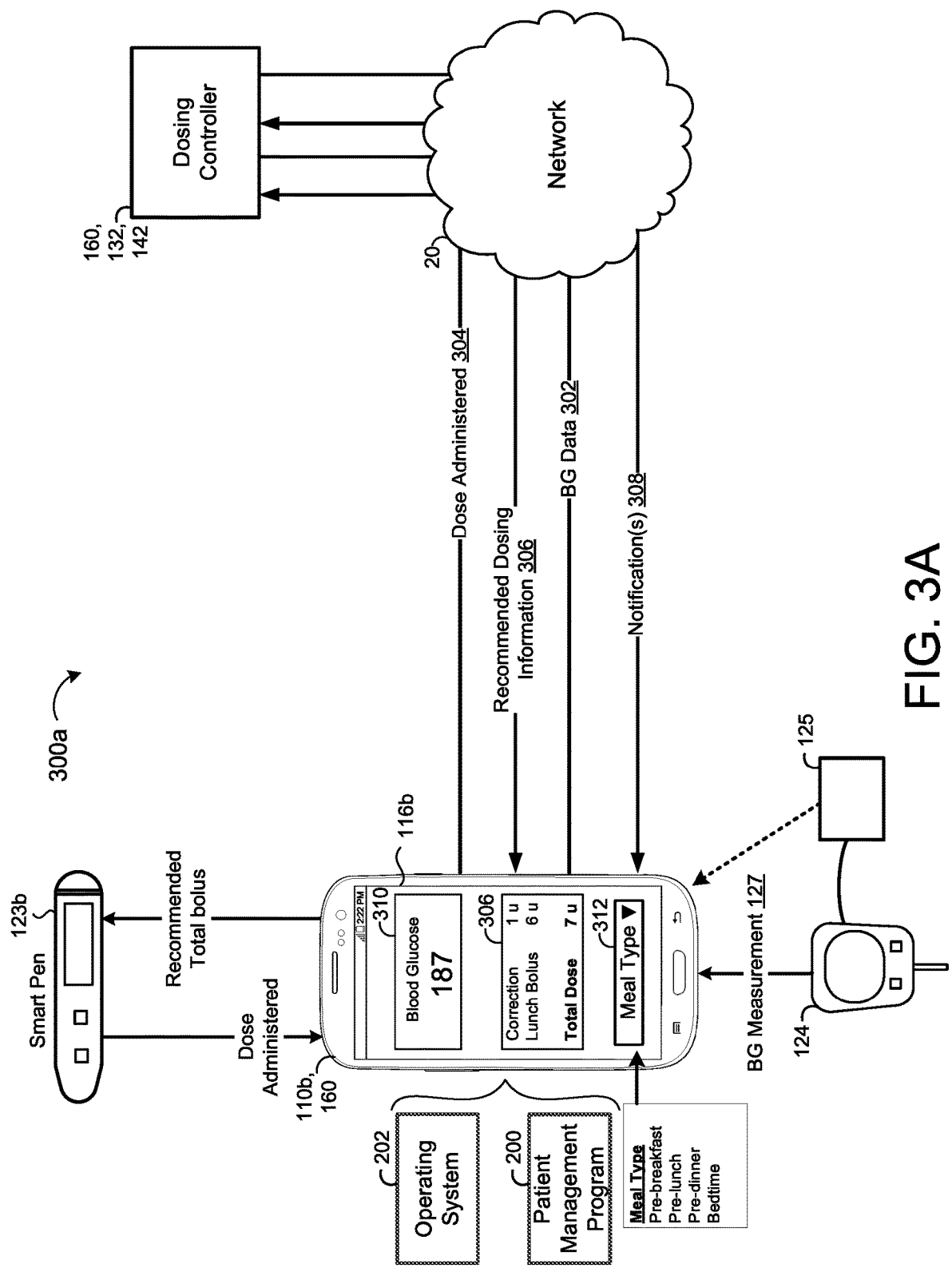
FIGS. 3A and 3B are schematic views of exemplary components of the system of FIG. 1.
Figure 3B:
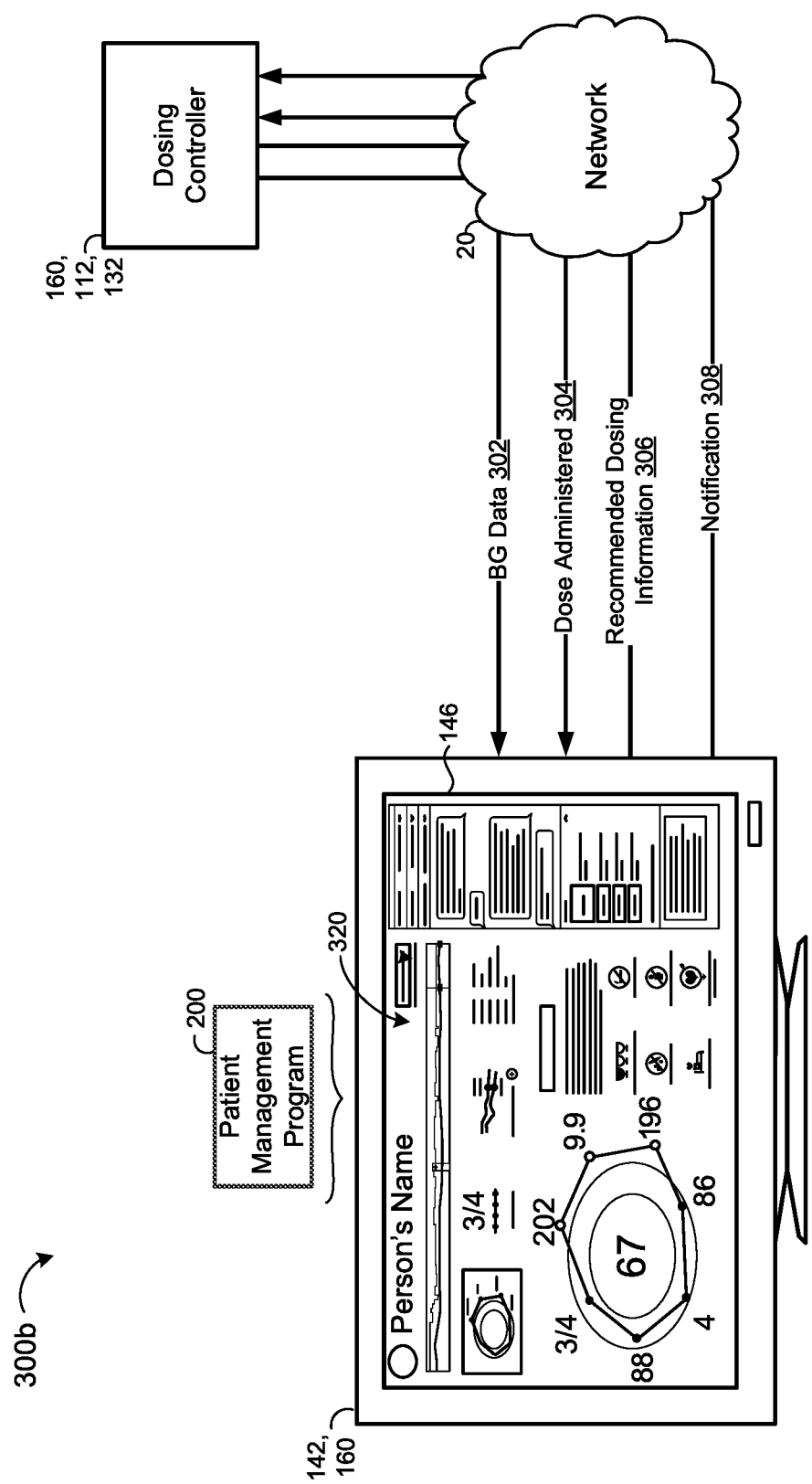

FIGS. 3A and 3B are schematic views 300a, 300b of exemplary components of the system of FIG. 1. Referring to FIG. 3A, in some implementations, the computing device 112b of the smart phone 110b executes the patient management program 200 (e.g., insulin management program) for communicating with the dosing controller 160 such that information can be communicated over the network 20 between the dosing controller 160 and the smart phone 110b. For example, the smart phone 110b may transmit blood glucose data 302 and a dose of insulin administered by the patient 10 (e.g., dose administered 304) to the dosing controller 160 and stored within the memory hardware 134, 144. The BG data 302 includes a BG measurement 127 and a BG time associated with a time of measuring each blood glucose measurement. In some examples, the dosing controller 160 executing on the user device 132, 142 transmits recommended dosing information 306 to the smart phone 110b based on the obtained blood glucose data and dose administered 304 by the patient 10. The dosing information 306 may include dosing parameters such as, but is not limited to: TargetBG, Correction Factor (CF), CIR for all day, CIR's for each meal, Recommended Breakfast Bolus, Recommended Lunch Bolus, Recommended Dinner Bolus, Recommended Basal doses, number of Basal doses per day, and Basal dose scheduled times. The dosing parameters may be adjusted automatically or manually initiated by the user 40 or patient 10. The dosing controller 160 may additionally transmit one or more notifications 308 to the smart phone 110b that causes the smart phone 110b to graphically display content associated with each notification 308 on the display 116b.

The patient devices 110 may use a variety of different operating systems 202. In examples where the patient device 110 is the smart phone 110b, the smart phone 110b may operate using an OS such as ANDROID® by Google, Inc., IOS® by Apple, Inc., or WINDOWS PHONE® by Microsoft Corporation. In an example where the user device 102 is a laptop or desktop computing device, the user device 102 may use an OS such as MICROSOFT WINDOWS® by Microsoft Corporation, MAC OS® by Apple, Inc., or LINUX® (LINUX® is the registered trademark of Linus Torvalds in the U.S. and other countries). The patient devices 110 may also interact with the dosing controller 160 using other operating systems.

The patient management program 200 enables the patient device 110 to interface with the dosing controller 160 executing on the user device 142 or the computing device 132 of the service provider 130. In some examples, the patient management program 200 is associated with an application dedicated to interfacing with the dosing controller 160 via the network 20. In other examples, the patient management program 200 is associated with a more general application, such as a web browser application. In any case, the patient management program 200 executing on the computing device 112 of the patient device 110 for communicating with the dosing controller 160 includes a graphical user interface that displays a blood glucose input field 310 on the display 116 for receiving a current blood glucose measurement input by the patient using a touchscreen, physical keyboard, a speech-to-text program, or other form of user input available on the patient device 110. Additionally or alternatively, the patient management program 200 may enable the patient device 110 (e.g., smart phone 110b) to communicate with the glucometer 124 for obtaining blood glucose measurements. For instance, the glucometer 124 and smart phone 110b may communicate via Bluetooth, infrared, cable, or any other communications. In some examples, the glucometer 124 communicates with a data translator 125, and the data translator 125 provides the blood glucose measurements from the glucometer 124 to the smart phone 110b. The GUI may display the blood glucose measurements communicated from the glucometer 124 or translator 125.

In some implementations, the smart phone 110b renders the BG measurement upon the display 116b and transmits the BG data including the BG measurement and the BG time to the dosing controller 160 via the network 20. In response to receiving the BG data from the smart phone 110b, the dosing controller 160 executing on the computing device 132, 142 may calculate a correction bolus (CB) using EQ. 2 based upon the current correction factor (CF) and Target BG stored within the memory 24, 134, 144. The CF and Target BG may be provided when a previous dosing parameter adjustment was transmitted to the smart phone 110b from the dosing controller 160. Thereafter, the dosing controller 160 transmits the CB within the recommended dosing information 306 to the smart phone 110b, and upon receiving the recommended dosing information 306, the patient management program 200 executing on the smart phone 110b causes the smart phone 110b to display the recommended dosing information 306 upon the display 116b.

In some examples, the GUI of the patient management program 200 provides a meal type selection box 312 that enables the patient 10 to select a meal type associated with the BG measurement and the BG time and transmits the selected meal type in the BG data 302 to the dosing controller 160 via the network 20. For instance, the meal type for a given BG measurement may include at least one of a pre-breakfast blood glucose measurement, a pre-lunch blood glucose measurement, a pre-dinner blood glucose measurement, or a bedtime blood glucose measurement. In some implementations, the dosing controller 160 determines a recommended meal bolus based on the meal type selected by the patient 10 and transmits the recommended meal bolus in the recommended dosing information 306 to the smart phone 110b via the network 20. For instance, the recommended dosing information 306 displayed upon the display 116 of the smart phone 110b may include the CB (e.g., Correction 1 u), the meal bolus (e.g., Lunch bolus 6 u), and a total recommended dose (e.g., 7 u) based on a sum of the CB and the meal bolus.

In some implementations, the insulin administration device 123 associated with the patient 10 includes a smart pump 123a or a smart pen 123b that is capable of communicating (e.g., syncing) with a patient device 110 such as a smart phone 110b. In the example shown, the smart pen 123b communicates with the smart phone 110b via Bluetooth, however, other wireless or wired communications are possible. In some examples, the smart pen 123b automatically dials in the total bolus for the doser 223b to administer. In some examples, the smart pen 123b receives a recommended total bolus dose from the smart phone 110b based on the recommended dosing information 306 transmitted from the computing device 142 of the dosing controller 160 via the network 20. In some examples, upon administration of an insulin dose by the smart pen 123b, the smart pen 123b transmits the value of the administered dose to the smart phone 110b for storage within memory 114a along with the associated BG measurement. In other examples, the patient 10 uses the GUI of the patient management program 200 to input the value of the dose administered 304. The smart phone 110b may transmit the dose administered 304 to the computing device 132, 142 of the dosing controller 160 via the network for storage within the memory hardware 134, 144.

Referring to FIG. 3B, in some implementations, the user device 142 of the clinic system 140 executes the patient management program 200 for communicating with the dosing controller 160 such that information can be communicated over the network 20 between the dosing controller 160 and the user device 142. For example, the user device 142 may receive the BG data 302 and the dose administered 304 from the dosing controller 160 via the network 20. In some examples, the computing device 112 of the patient device 110 executes the dosing controller 160 and transmits the BG data 302 and/or the dose administered 304 directly to the user device 142. In other examples, the dosing controller 160 executes on the computing device 132 of the service provider 130 such that the computing device 132 receives the BG data 302 and/or the dose administered 304 from the patient device 110 and provides the BG data 302 and/or the dose administered 304 to the user device 142.

The user device 142 may transmit updates to the recommended dosing information 306 to the dosing controller 160 via the network 20 and/or transmit the one or more notifications 308 to the dosing controller 160 for display on a target patient device 110. For example, notifications 308 can include a low blood glucose alert notification 308 when a patient's current BG measurement is less than a hypoglycemia blood glucose value (e.g., obtained from memory hardware 20, 134, 144) or a blood glucose request notification 308 when a current time is within a scheduled blood glucose time interval for the patient 10 that requires a current BG measurement.

In some implementations, the patient management program 200 is configured to display on the display screen 146 in communication with the user device 142 a GUI having historical blood glucose and dosing information 320 for one or more patients 10. The historical blood glucose and dosing information 320 may include a trend window 1102 (FIGS. 11A-11E) of obtained BG measurements on a timeline. In some examples, the patient management program 200 is configured to receive magnifying inputs in the trend window 1102 from a user 40 (e.g. HCP) for a magnification window 1104 (FIGS. 11A-11E) superimposed on a segment of the timeline to specify a date range for a magnified window 1106 (FIGS. 11A-11E). Here, the GUI of the patient management program 200 may display the magnified window 1106 including the BG measurements of the patient 10 from the specified date range.

Figure 4A:
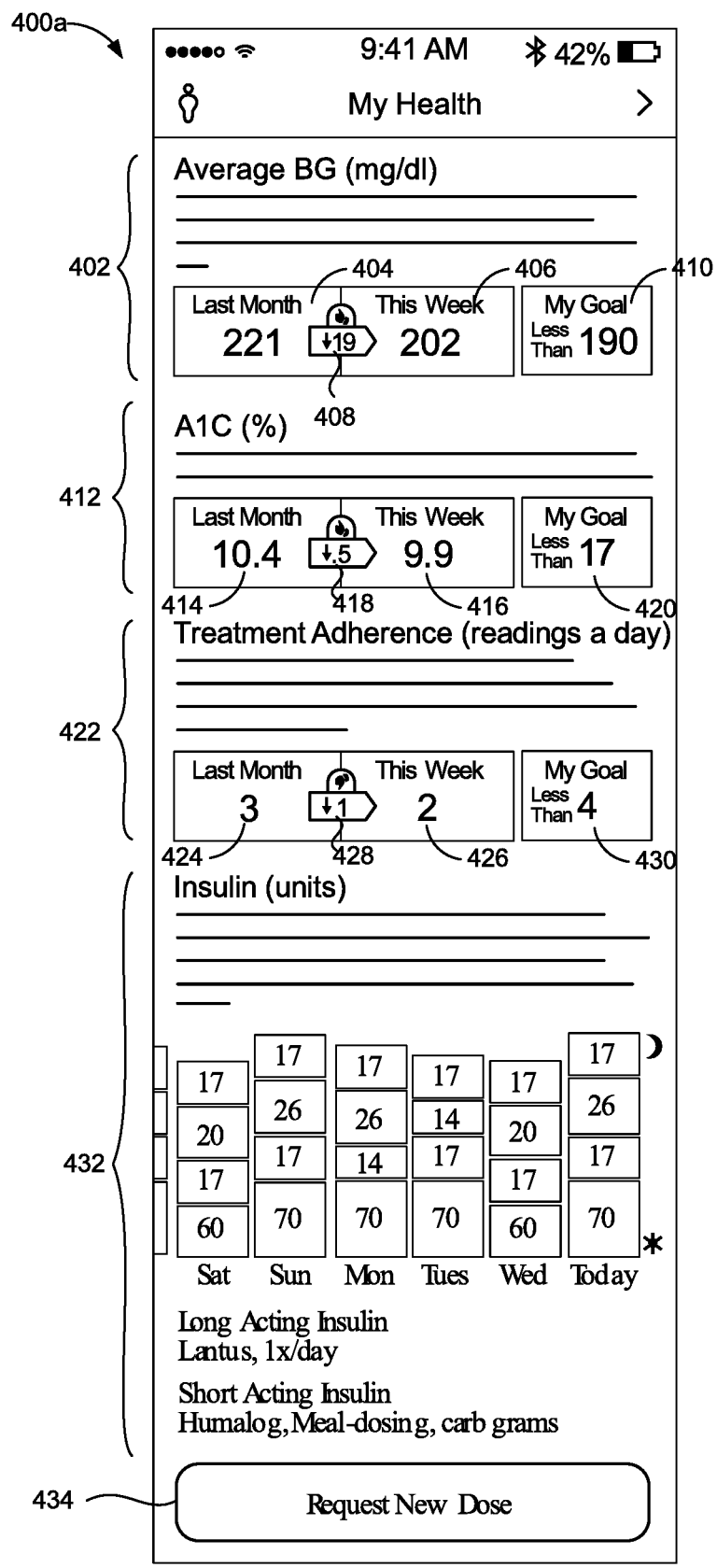

FIGS. 4A-4C show schematic views 400a-c of example GUIs of the patient management program 200 displayed on the display 116 of the patient device 110 for viewing historical blood glucose and dosing data for a patient 10. Referring to FIG. 4A, the example GUI displays average BG value information 402, average hemoglobin A1c information 412, treatment adherence information 422, and insulin information 432.

The average BG value information 402 includes a last month's average BG value 404, a current week's average BG value 406, and a trending graphic 408 indicating a magnitude that the current week's average BG value 406 increases or decreases from last month's average BG value 404. The BG value information 402 may also display a BG value goal 410 indicating the target BG value for the patient 10. The blood glucose parameters (e.g., SubQ parameters 216a) for the patient 10 may include the BG value goal 410 for access by the patient management program 200. The BG value information 402 may also include educational information related to the correlation between maintaining blood glucose levels and health of the patient. For example, the education information may state that "Lowering your blood sugar will help you feel better and have more energy in the short run, and lower your chances of eye, kidney, liver, and heart disease in the long run."

The average A1c information 412 includes a last month's average A1c value 414, a current week's average A1c value 416, and a trending graphic 418 indicating a magnitude that the current week's average A1c value 416 increases or decreases from last month's average Alec value 414. The A1c information 412 may also display an A1c value goal 420 for the patient which may be obtained from the SubQ parameters 216a input to the system 100 by the HCP 40 and accessible by the patient management program 200. The A1c value information 412 may also include educational information related to the correlation between lower A1c values and health of the patient 10. For example, the education information may state that "Less than a 1 percentage point drop in A1C can lead to 45% decreased risk of death from cardiovascular disease.

The adherence information 422 is associated with a number of times per day (e.g., a number of readings per day) the patient 10 checks/measures his or her blood glucose level using the glucometer 124. The adherence information 422 includes a last month's average number of readings per day 424, a current week's average number of readings per day 426, and a trending graphic 428 indicating a magnitude that the current week's average number of readings per day 426 increases or decreases from last month's average number of readings per day 424. The adherence information 422 may also display an adherence goal 430 indicating a target number of times the patient 10 should measure/check his or her blood sugar. The adherence information 422 may also include education information related to the correlation between increasing the number of blood glucose readings per day and managing blood glucose values. For example, the education information may state that "Checking your blood sugar regularly will help us prescribe the right dosage for you. Sticking with this insulin regimen will help you tightly control your blood sugar and feel better."

The insulin information 432 may display an insulin dosing regimen for the patient 10 as prescribed by the HCP. For instance, the insulin dosing regimen may include a daily schedule of basal and meal doses the patient 10 is prescribed to administer each day. The insulin dosing regimen may correspond to the insulin dosing information 306 the dosing controller 160 transmits to the patient device 110 based on the BG Data 302 the dosing controller 160 obtains from the patient device 110, as set forth above with respect to FIG. 3A. For example, the dosing controller 160 may automatically adjust the patient's 10 insulin dosing regimen during predetermined intervals (e.g., daily, weekly, every two weeks, etc.) based on the BG data 302 obtained from the patient device 110. Similarly, the HCP 40 may analyze the patient's 10 BG data 302 over a specified time range and adjust the patient's 10 insulin dosing regimen accordingly. FIG. 4A shows the GUI of the patient management program 200 displaying a chart of a daily frequency of insulin distribution (e.g., 4 doses per day) and a number of units administered by the patient 10 for each dose. For example, the patient 10 may be prescribed a frequency of insulin distribution (e.g., as indicated in the patient SubQ information 216a) that includes a basal dose in the morning and breakfast, lunch, and dinner meal boluses. The insulin information 432 may also display an insulin type and frequency of distribution for the patient's long-acting basal insulin (e.g., Lantus, 1×/day) along with an insulin type for the patient's short acting bolus insulin (e.g., Humalog, Meal-dosing, carb grams). In some configurations, the GUI of the patient management program 200 includes a "Request New Dose" patient-selectable link 434 that allows the patient 10 to request a new dose of insulin from the dosing controller 160 when the patient 10 selects the Request New Dose patient-selectable link 434. Accordingly, the dosing controller 160 may calculate a new insulin dosing regimen for the patient 10 in response to the patient selecting the "Request New Dose" user-selectable link 434 displayed by the GUI of the patient management program 200 on the display 116 of the patient device 110.

Referring to FIG. 4B, the example GUI displays a blood glucose screen providing the patient's BG data 302 based on the BG measurements and BG times obtained by the glucometer 124 and provided to the patient device 110 and/or dosing controller 160. In some implementations, the patient management program 200 determines a representative average BG value for each scheduled blood glucose time interval for the patient during a specified time range. In these implementations, the GUI of the patient management program 200 displays a representative average BG value graph 440 indicating the representative average BG value for each of the scheduled blood glucose time intervals during the specified time range. For example, FIG. 4B shows the graph 440 including the representative average BG value determined by the patient management program 200 for each one of Breakfast, Lunch, Dinner, and Bedtime scheduled blood glucose time intervals during a current week. The graph 440 may graphically display the representative average BG value for each BG time interval (e.g., 201 for Breakfast; 165 for Lunch; 198 for Dinner; 215 for Bedtime) and a profile line 442 extending through each value. The graph 440 may also provide the target BG range 444 (e.g., "Goal 70-100") for the patient 10. In some examples, the profile line 442 includes different representations based on the representative average BG value. For instance, the profile line 442 may change color for representative average BG values outside the target BG range 444. For instance, FIG. 4B shows the profile line 442 including a different color for the representative average BG value of 165 during lunch than the higher representative average BG values of 201, 198, and 215 for the respective ones of Breakfast, Dinner, and Bedtime. In some implementations, the graph 440 graphically displays low BG measurements (e.g., BG measurements less than the hypoglycemia blood glucose value) as well as high BG measurements (e.g., BG measurements greater than the hyperglycemia blood glucose value).

In some implementations, the GUI of the patient management program 200 also graphically displays daily BG data 446 for the patient 10 indicating the patient's BG measurement obtained by the patient's 10 glucometer 124, the BG time for each BG measurement, and the BG time interval for each BG measurement. For example, the GUI may display the daily BG data 446 for a current day (e.g. Today) and include BG values for BG time intervals of Before Breakfast, After Breakfast, After Lunch After Dinner, and Bedtime. The GUI may display the BG measurements as different representations based on the value for each BG measurement. For example, the value of each BG measurement displayed may be color coordinated based upon a range of BG values the corresponding BG measurement falls into. Moreover, the daily BG data 445 may also provide an upward arrow next to BG measurements that exceed an upper limit of the BG target range or a downward arrow next to BG measurements that are less than a lower limit of the BG target range.

Referring to FIG. 4C, the example GUI displays an insulin dosing screen indicating the number of units of insulin administered by the patient 10 during each scheduled time interval. In some examples, the administration device 123 communicates the number of doses administered by the patient 10 to the patient device 110 and the patient device 110 transmits the dose administered 304 (FIG. 3A) to the dosing controller 160. In other examples, the patient management program 200 enables the patient to input the number of doses administered by the patient 10 directly to the patient device 110. Accordingly, the GUI of the patient management program 200 displays an insulin dosing graph 450 indicating a number of units of insulin administered by the patient 10 for each scheduled time interval during a specified time range. For example, FIG. 4C shows the graph 450 including a basal profile line 452, a breakfast bolus profile line 454, a lunch bolus profile line 454, and a dinner bolus profile line 456. Here, each profile line 452-458 indicates the number of units of insulin administered by the patient during each day during the specified time range (e.g., This Week).

In some implementations, the GUI of the patient management program 200 also graphically displays daily insulin dosing data 460 for the patient 10 including the number of units of insulin for each scheduled dose, a time interval for each scheduled dose, and a time for each scheduled dose administered by the patient 10. For example, the GUI may display the daily insulin dosing data 460 for a current day (e.g., Today) and include a number of units of insulin for scheduled doses of Fasting (70 units), Breakfast (17 units), Lunch (26 units), and Dinner (17 units). The insulin dosing data 460 may include the type of insulin for each scheduled dose. For instance, FIG. 4C shows the insulin dosing data 460 indicating the insulin type for the Fasting interval is Lantus (e.g., long-acting basal) while the insulin type for the Breakfast, Lunch, and Dinner intervals is Humalog (e.g., short-acting bolus). The insulin dosing data 460 also indicates when a scheduled dose is skipped by the patient when the dosing controller 160 fails to receive the dose administered 302 from the patient device. For example, the insulin dosing data 460 of FIG. 4C indicates that the scheduled dose for Dinner is skipped.

Figures 5A, 5B:
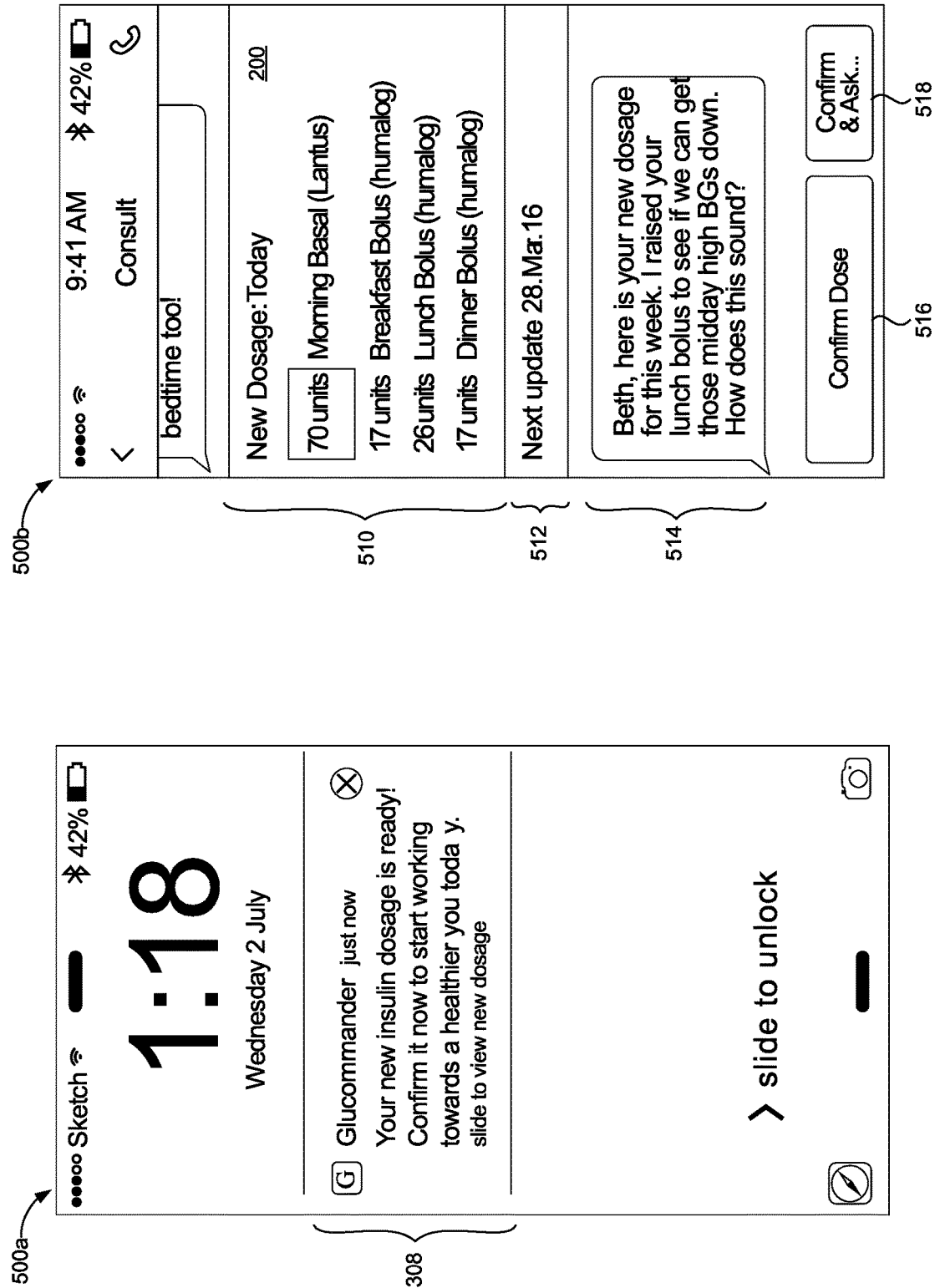
FIGS. 5A and 5B are schematic views of example graphical user interfaces displaying insulin dosing information for a patient.

FIGS. 5A and 5B show schematic views 500a, 500b of example GUIs of the patient management program 200 displayed on the display 116 of the patient device 110 for viewing and confirming a recommended insulin dosing regimen for the patient 10. The HCP 40 may prescribe the recommended insulin dosing regimen for the patient 10 based upon the BG data 302 associated with the patient 10. The HCP 40 and/or the dosing controller 160 may adjust the recommended insulin dosing regimen in real-time using one or more BG measurements for the patient 10 obtained by the dosing controller. Similarly, the HCP 40 and/or the dosing controller 160 may adjust or update the recommended insulin dosing regimen during predetermined intervals (e.g., daily, every 3 days, weekly, every two weeks, etc.). FIG. 5A shows the GUI of the patient management program 200 displaying a new insulin dosage notification 308 on the display 116 of the patient device 110 (e.g., smart phone 110b) that notifies the patient 10 when a new recommended insulin dosing regimen is ready for the patient 10 to view and confirm. For example, in response to receiving a notification 308 (FIG. 3A) from the dosing controller 160 (e.g., user device 142 or computing device 132) via the network 20, the patient management program executing on the computing device 112 may cause the patient device 110 to display the new insulin dosage regimen notification 308 on the display 116. In some examples, the new insulin dosage regimen notification 308 includes a user selectable link associated with data, such that when the patient 10 selects the link 308, the patient management program 200 causes the patient device 110 to display an insulin dosing regimen screen providing the new insulin dosage regimen for the patient.

FIG. 5B shows the GUI of the patient management program 200 displaying the insulin dosing regimen screen in response to the patient selecting the user selectable link associated with the new insulin dosage notification 308 of FIG. 5A. The insulin dosing regimen screen displays the new insulin dosing regimen 510 for the patient indicating a daily frequency of distribution and a number of units of insulin for each insulin dose of the distribution. For example, the new insulin dosing regimen 510 of FIG. 5B includes 4 doses of insulin per day for morning basal (e.g., 70 units of Lantus), breakfast bolus (e.g., 18 units of Humalog), lunch bolus (e.g., 26 units of Humalog), and dinner bolus (e.g., 17 units of Humalog). The patient management program 200 may render the new insulin dosing regimen 510 on the display 116 in the form of a message or communication from the HCP 40 that includes a next update message 512 and a personal message 514 for the patient 10 associated with the new insulin dosing regimen 510. For example, FIG. 5B shows the personal message 514 stating "I raised your lunch bolus to see if we can get those midday high BGs down. How does this sound?" In some implementations, the GUI of the patient management program 200 displays a Confirm Dose user-selectable link 516 that enables the patient 10 to confirm the new insulin dosing regimen 510 when the patient 10 selects the Confirm Dose user-selectable link 516. Accordingly, the user device 142 associated with the HCP 40 may receive a message through the network 20 from the patient device 110 indicating the patient 10 has confirmed the new insulin dosing regimen 510 in response to the patient 10 selecting the Confirm Dose user-selectable link. The GUI of the patient management program 200 may also display a Confirm & Ask user-selectable link 518 that enables the patient 10 to inquire the HCP 40 about the new insulin dosing regimen 510 when the patient 10 selects the Confirm & Ask user-selectable link 518. By selecting, the Confirm & Ask user-selectable link 518, the patient management program 200 may cause the patient device 110 to display a text box for the patient 10 to input textual message for the HCP 40 to answer and/or cause the patient device 110 to initiate a phone call with the HCP 40 when the patient device 110 is capable of voice calls.

Figures 6A, 6B, 6C:
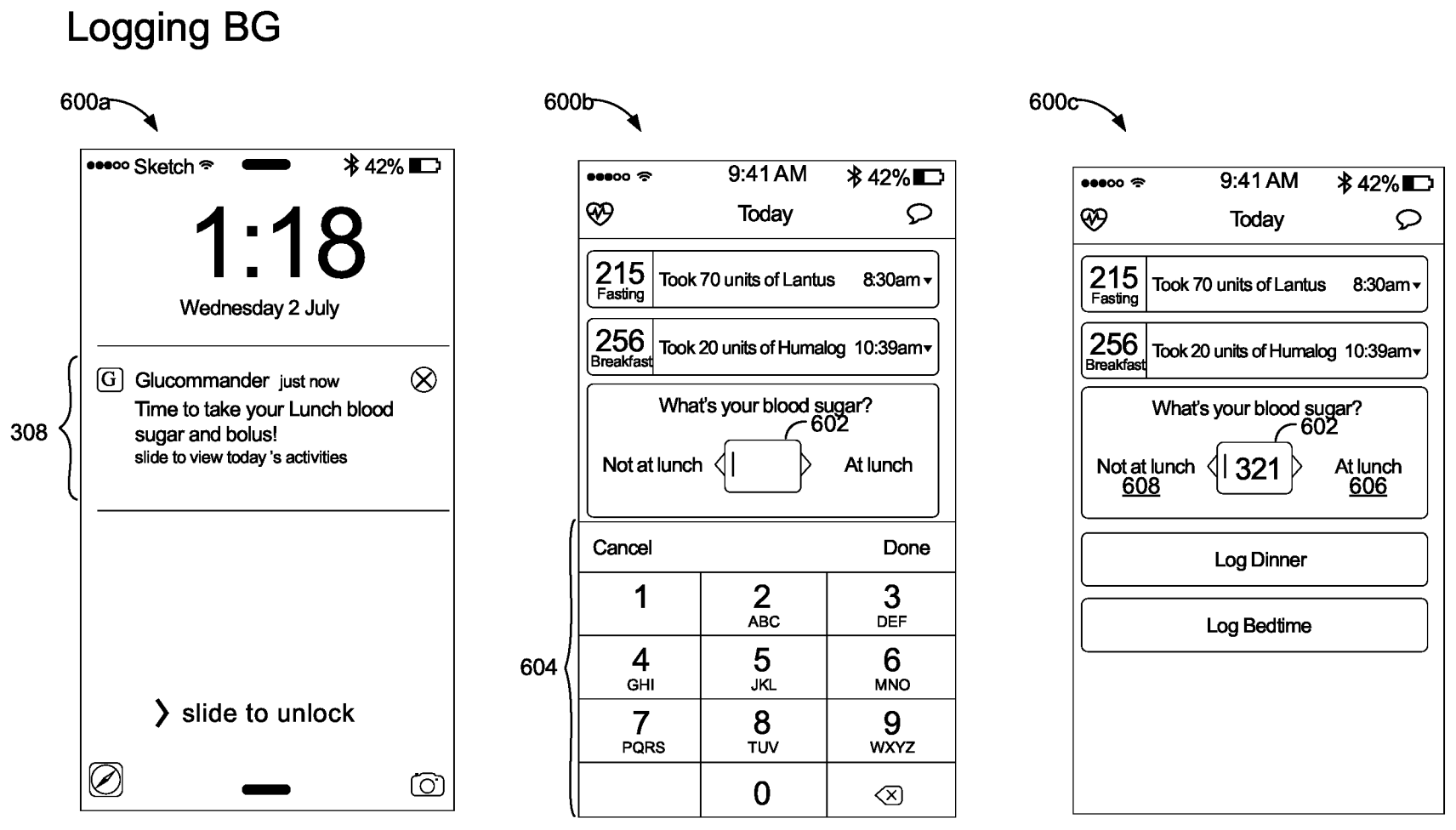

FIGS. 6A-6C show schematic views 600a-c of example GUIs of the patient management program 200 displayed on the display 116 of the patient device 110 for logging BG measurements measured by the patient's 10 glucometer 124. The SubQ information 216a input to the patient management program 200 may include scheduled BG time intervals each indicating a time interval requiring a BG measurement for the patient 10. For example, the scheduled BG time intervals may include a pre-breakfast BG measurement, a pre-lunch BG measurement, a pre-dinner BG measurement, and/or a bedtime BG measurement. In some implementations, the dosing controller 160 determines whether a current time is within one of the scheduled BG time intervals requiring a BG measurement, and when the current time is within one of the scheduled BG time intervals and the corresponding BG measurement has not been received, the dosing controller 160 transmits a blood glucose request notification 308 to the patient device 110 during the scheduled BG time interval. For example, the user device 142 may implement the dosing controller 160 and transmit the blood glucose request notification 308 to the smart phone 110b associated with the patient 10 during the scheduled BG time interval, as shown in FIG. 3A. When the patient device 110 (e.g., smart phone 110b of FIG. 3A) receives the blood glucose request notification 308 from the dosing controller 160, the patient management program 200 executing on the computing device 112 of the patient device displays the blood glucose request notification 308 on the display 116 (e.g., patient screen).

FIG. 6A shows the GUI of the patient management program 200 displaying the blood glucose request notification 308 instructing the patient to attain a current blood glucose measurement for the scheduled Lunch BG time interval. In some examples, the blood glucose request notification 308 includes a user-selectable link associated with data, such that when the patient 10 selects the link 308, the patient management program 200 causes the patient device 110 to advance to a patient screen for inputting the current blood glucose measurement for the scheduled BG time interval.

FIG. 6B shows the GUI of the patient management program 200 displaying a BG input field 602 (e.g., "BG input box") enabling the patient 10 to input the current BG measurement for the scheduled BG time interval. The patient management program 200 may display a touchscreen keypad 604 for use by the patient 10 to input the current BG measurement. Alternatively, the patient 10 may input the current BG measurement to the BG input field 602 using the keyboard 119 and/or via speech recognition techniques. The patient management program 200 may display the BG input field 602 and touchscreen keypad 604 in response to the patient selecting the user-selectable link associated with the blood glucose request notification 308 displayed by the example GUI of FIG. 6A or the patient 10 may navigate to the example GUI of FIG. 6B when the patient 10 desires to enter a BG measurement. In other examples, the glucometer 124 automatically transmits a current BG measurement to the patient device 110 to cause the patient management program to render the received BG measurement in the BG input filed 602 without requiring input by the patient 10.

FIG. 6C shows the current BG measurement (e.g., 321 mg/dl) input to the BG input field 602 and the GUI of the patient management program 200 displaying user-selectable link 606, 608 that enables the patient 10 to log the current BG measurement as corresponding to the scheduled BG time interval (e.g. "At Lunch") when the patient 10 selects the user-selectable link 606 or as not corresponding to the scheduled BG time interval (e.g., "Not at Lunch") when the patient 10 selects the user-selectable link 608. In response to the patient 10 selecting the user-selectable link 606 to log the current BG measurement as corresponding to a scheduled BG time interval, the patient management program 200 may cause the patient device 110 to display the example GUIs of FIGS. 7A-7D or the example GUIs of FIGS. 8A and 8B for calculating a meal bolus for the patient 10 associated with the scheduled BG time interval. As used herein, the user-selectable link 606 may correspond to a patient-selectable meal type button 606 indicating a meal type (e.g., Lunch) when the patient is consuming a meal based on the BG time associated with the current BG measurement input to the BG input field 602. Conversely, in response to the patient 10 selecting the user-selectable link 608 to log the current BG measurement as not corresponding to a scheduled BG time interval, the patient management program 200 may cause the patient device 100 to display the example GUIs of FIGS. 9A and 9B for requesting the patient 10 to provide rational for checking/measuring the current BG measurement and/or calculate a correction dose if necessary based on the current BG measurement.

The GUI of FIGS. 6B and 6C may correspond to a patient log screen showing a log of BG measurements, corresponding BG times, and/or doses of insulin administered by the patient 10 in addition to the BG input field 602. For instance, during a scheduled Fasting BG time interval, the patient 10 logged a BG measurement equal to 215 mg/dl and administered 70 units of Lantus insulin for the patient's basal dose. Similarly, during a scheduled Breakfast BG time interval, the patient 10 logged a BG measurement equal to 256 mg/dl and administered 20 units of Humalog insulin for the patient's breakfast bolus. The patient's breakfast bolus may include a sum of a correction bolus and a meal bolus.

FIGS. 7A-7D show schematic views 700a-d of example GUIs of the patient management program 200 displayed on the display 116 of the patient device 110 for calculating a meal bolus for the patient 10 associated with the scheduled BG time interval when the patient 10 selects the meal type button 606 (e.g., user-selectable link 606). The patient management program 200 may augment an area of the GUI including the meal type button 606 when the patient selects the meal type button 606 and prompt the patient to input a meal size for the meal type associated with the selected meal type button 606. For example, the example GUI of FIGS. 7A and 7B highlights an area around the meal type button 606 indicating the patient 10 is consuming or about to consume Lunch. The meal type button 606 may correspond to breakfast or dinner in other examples.

Figures 7A, 7B:
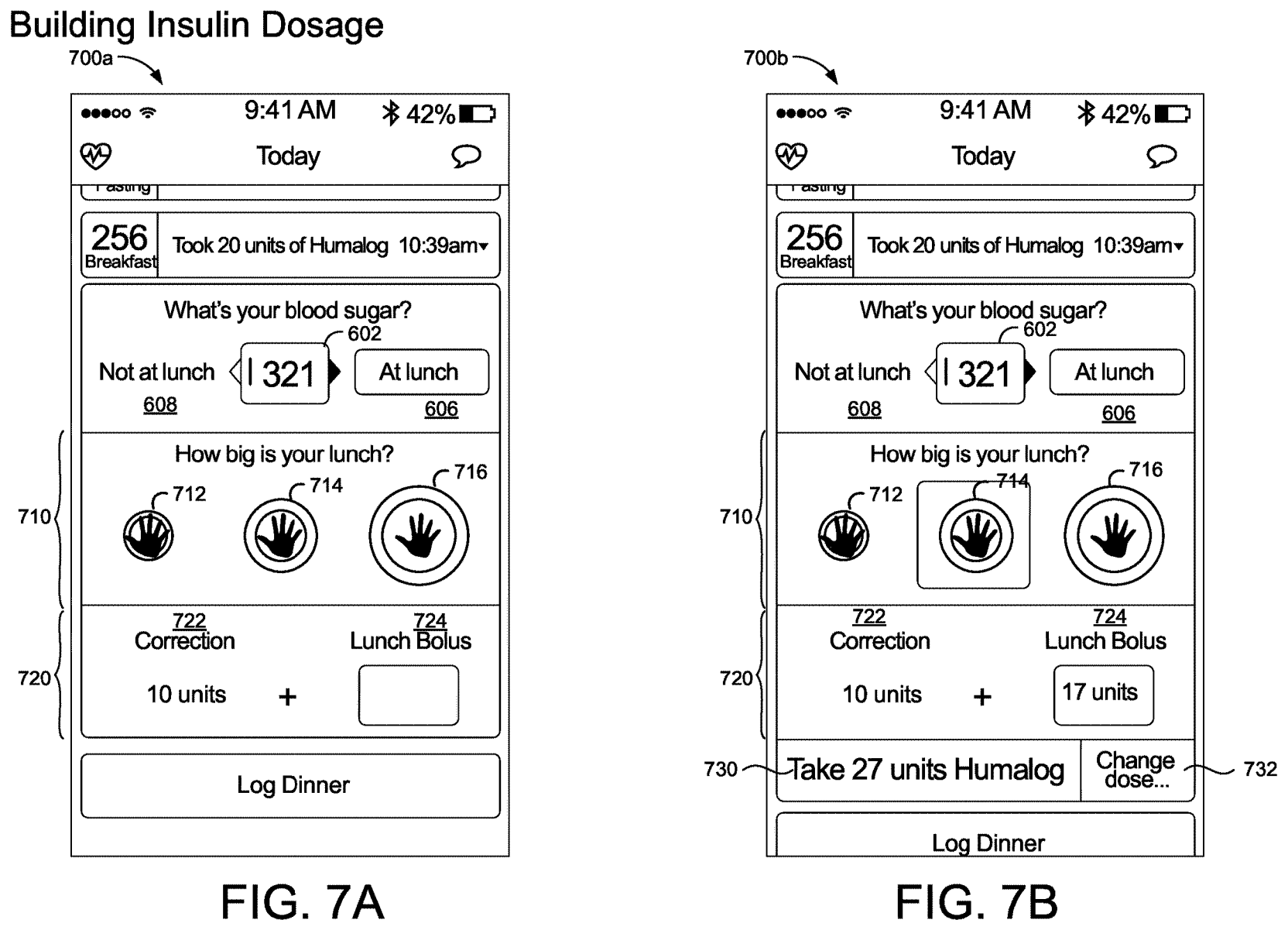

FIG. 7A shows the GUI rendering a meal size window 710 for the selected meal type (e.g., Lunch) that requests the patient 10 to input the meal size for the selected meal type. In some examples, the meal size window 710 includes user-selectable links 712, 714, 716 each including a respective image that corresponds to a size of the patient's meal. Each user-selectable link 712, 714, 716 may be referred to as a patient-selectable meal size button indicating a respective meal size associated with the selected meal type. For instance, the meal size button 712 corresponds to a small meal size, the meal size button 714 corresponds to a medium meal size, and the meal size button 716 corresponds to a large meal size. Accordingly, the GUI of the patient management program 200 enables the patient 10 to select one of the meal size buttons 712, 714, 716 to input the meal size for the meal type and cause the patient device to transmit the input meal size to the dosing controller 160. The dosing controller 160 may execute on any of the computing devices 112, 132, 142.

The example GUI of FIG. 7A also renders a recommended insulin dose window 720 for the selected meal type which provides a correction bolus graphic 722 indicating a value of the correction dose for the patient 10 to administer. The dosing controller 160 may determine the correction bolus using Eq. 2 based on the current BG measurement input to the BG input field 602 and provide the correction bolus to the patient device 110 in the recommended dosing information 306 transmitted to the patient device 110. For instance, the correction bolus graphic 722 in the example of FIG. 7A includes a correction bolus equal to 10 units.

FIG. 7B shows the patient management program 200 augmenting an area of the GUI including the meal size button 712, 714, 716 selected by the patient 10. For example, the GUI highlights an area around the meal size button 714 indicating a "medium" meal size associated with the selected meal type (e.g., Lunch). The patient management program 200 may cause the patient device 110 to transmit the input meal size to the dosing controller 160 in response to the patient 10 selecting appropriate meal size button 712, 714, 716. Thereafter, the dosing controller 160 determines a recommended meal bolus for the patient 10 based on the meal size and meal type selected by the patient 10 (e.g., by selecting buttons 606 and 714) and transmits the recommended meal bolus to the patient device 110. For instance, the dosing controller 160 may transmit the recommended meal bolus in the recommended dosing information 306 to the patient device 110 via the network 20. In some examples, in response to receiving the recommended meal bolus (e.g., contained in the recommended dosing information 306) at the patient device 110, the patient management program 200 causes the recommended insulin dose window 720 displayed by the GUI to provide a meal bolus graphic 724 indicating a value of the meal bolus (e.g., Lunch meal bolus) for the patient 10 to administer. For instance, the meal bolus graphic 724 in the example of FIG. 7B includes a Lunch meal bolus equal to 17 units.

Upon displaying the values for the correction bolus and meal bolus in corresponding ones of the correction bolus graphic 722 and the meal bolus graphic 724, the GUI of the patient management program 200 displays a recommended total dosage of insulin for the patient based on a sum of the values of the recommended meal bolus and the correction dose. FIG. 7B shows the GUI displaying a patient-selectable total dosage button 730 that instructs the patient to administer the recommended total dosage of insulin (e.g., 27 units of Humalog based on the sum of the correction bolus and the meal bolus) and enables the patient 10 to confirm the recommended total dosage of insulin by selecting the total dosage button 730. Here, the patient management program 200 causes the patient device 110 to transmit the recommended total dosage of insulin as the dose administered 304 to the dosing controller 160 so that the total dosage of insulin for the selected meal type (e.g., Lunch) is logged and stored within the memory hardware 24, 114, 134, 144. Conversely, the GUI also displays a patient-selectable change dosage button 732 that permits the patient to change the value of the total dosage of insulin recommended by the dosing controller when the patient 10 selects the change dosage button 732.

Figure 7D:
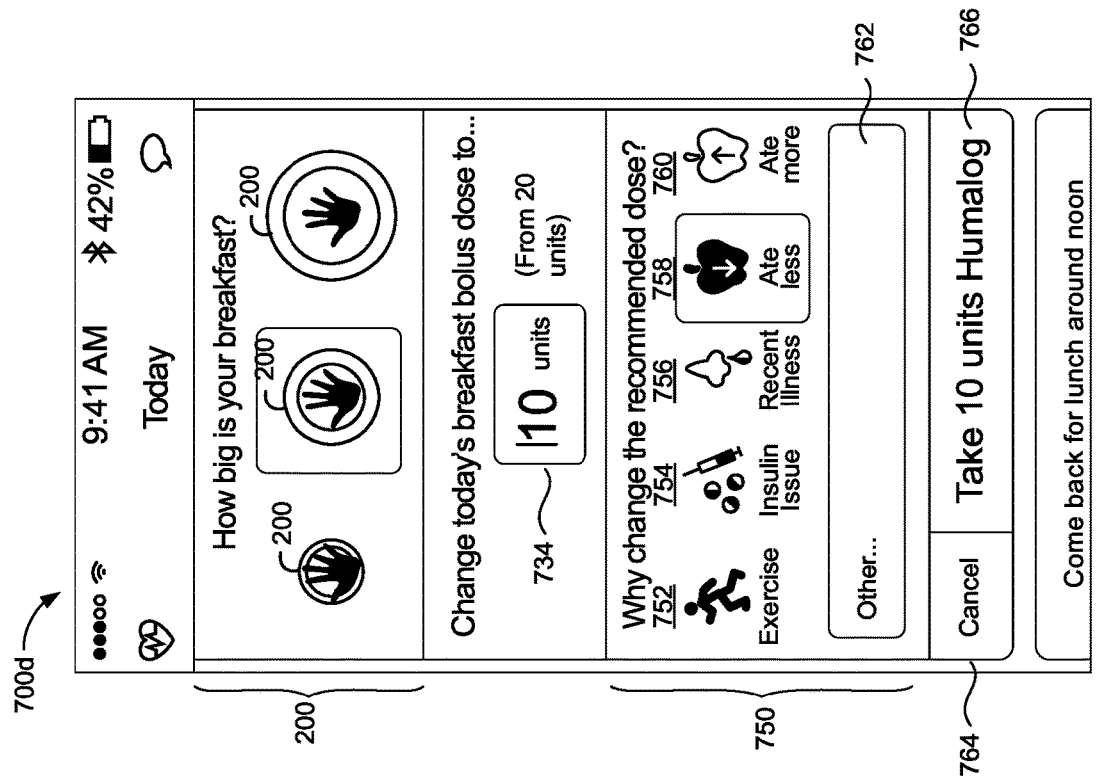
Figure 7C:
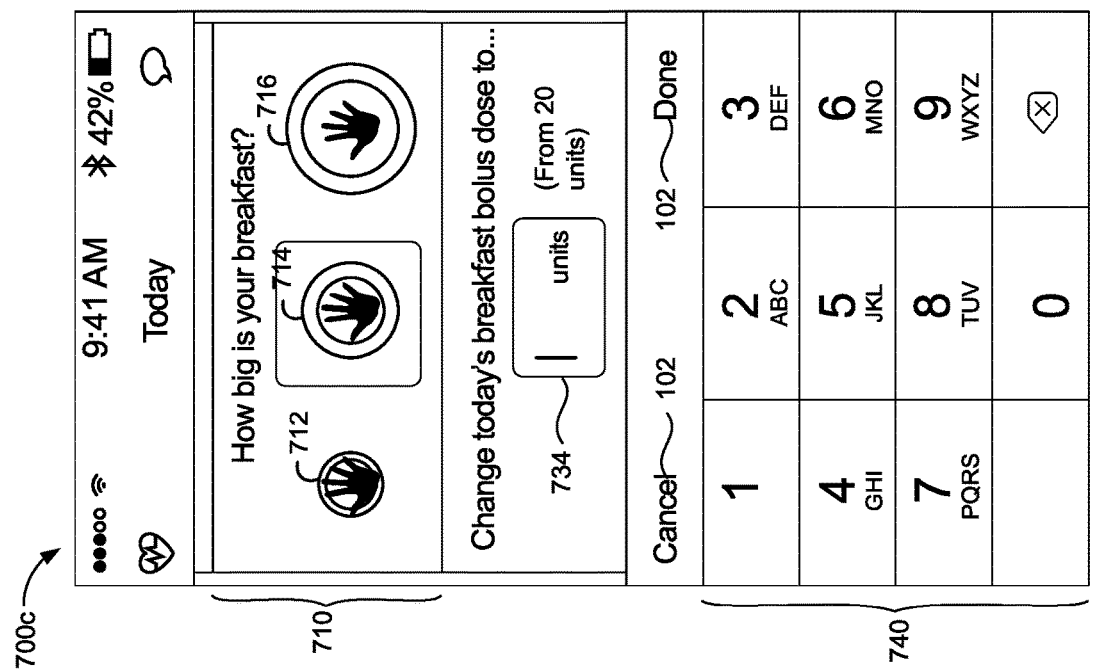

The example GUI of FIG. 7C renders a change dosage input field 734 that enables the patient 10 to change the recommended total dosage of insulin by inputting a new value in the change dosage input field 734 in response to the patient 10 selecting the change dosage button 732 in the example GUI of FIG. 7B. Moreover, the patient management program 200 may display a touchscreen key pad 740 for use by the patient 10 to input the new value in the change dosage input field 734. Alternatively, the patient 10 may input the new value to the change dosage input field 734 using the keyboard 119 and/or via speech recognition techniques.

Referring to FIG. 7D, in some implementations, the GUI of the patient management program 200 renders a change dosage rational window 750 in response to the new value input to the change dosage input field 734. The change dosage rational window 750 prompts the patient 10 to provide rational as to why the patient 10 has changed the recommended total dosage of insulin. For example, the change dosage rational window 750 may include one or more patient-selectable links 752, 754, 756, 758, 760 each including link data (e.g., text and/or images) associated with a corresponding rational for changing the recommended total dosage of insulin. For instance, patient selectable link 752 indicates the patient 10 is exercising, patient-selectable link 754 indicates the patient 10 is currently having insulin issues, patient-selectable link 756 indicates the patient 10 has a recent illness, patient-selectable link 758 indicates the patient 10 consumed less food than indicated by the meal size input, and patient-selectable link 760 indicates the patient 10 consumed more food than indicated by the meal size input. The patient management program may also augment an area of the GUI including the patient-selectable link 752-760 selected by the patient 10. For example, the GUI highlights an area around the patient-selectable link 758 indicating the patient's rational for changing the total dosage of insulin is due to the patient consuming less food than previously indicated by the meal size input. The patient management program 200 may also display a rational text box for permitting the patient 10 to input the rational for changing the recommended dosage of insulin if none of the links 752-760 describe the rational for changing the dose.

FIG. 7D also shows the GUI displaying a patient-selectable total changed dosage button 766 that instructs the patient to administer the new dosage of insulin (e.g., 10 units of Humalog based on the new value input to the change dosage input field 734) and enables the patient 10 to confirm the new dosage of insulin by selecting the changed dosage button 766. Here, the patient management program 200 causes the patient device 110 to transmit the new value for the total dosage of insulin as the dose administered 304 to the dosing controller 160 so that the new total dosage of insulin for the selected meal type (e.g., Lunch) is logged and stored within the memory hardware 24, 114, 134, 144. Conversely, the GUI also displays a patient-selectable canceled dosage button 732 that permits the patient to cancel the new value input to the change dosage input field 734.

Figure 8B:
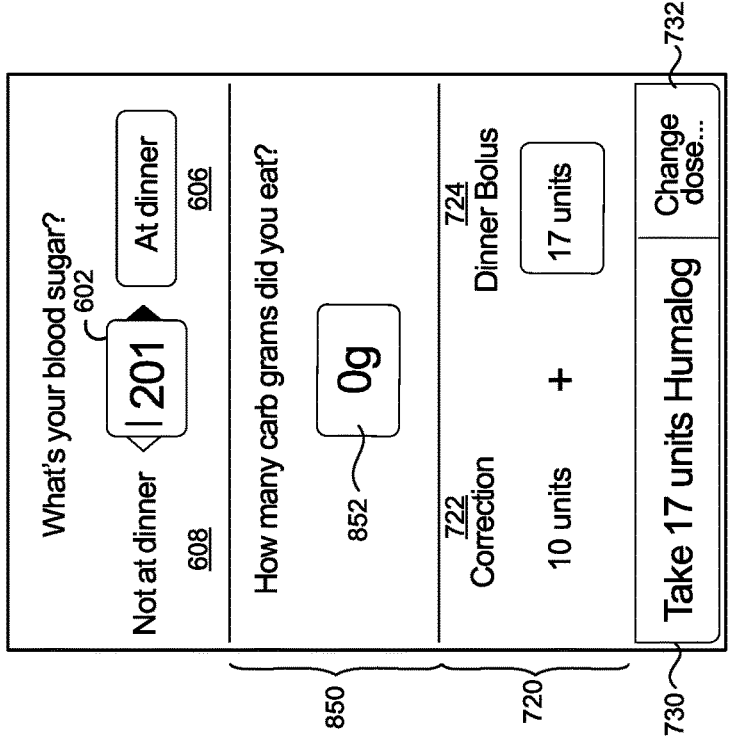
FIGS. 8A and 8B are schematic views of example graphical user interfaces for determining a meal bolus for a patient.
Figure 8A:
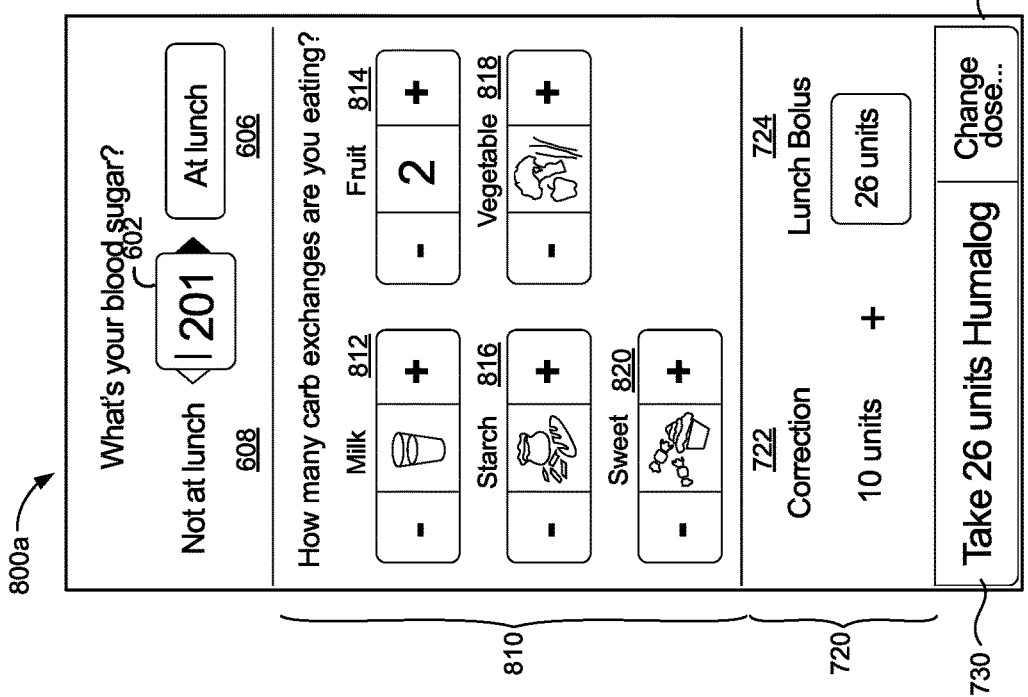

In some implementations, rather than the patient inputting the meal size to the patient device 110 by selecting one of the multiple meal size buttons 712, 714, 716 displayed on the patient screen as set forth above with respect to FIGS. 7A and 7B, the patient 10 inputs the meal size by inputting a number of carbohydrate exchanges associated with the meal type. As used herein, one carbohydrate exchange refers to 15 grams of carbohydrate. For instance, a piece of bread generally contains 15 grams of carbohydrate and therefore corresponds to one carbohydrate exchange. FIG. 8A provides a schematic view 800a of an example GUI of the patient management program 200 rendering a carbohydrate exchange window 810 for the selected meal type (e.g., Lunch) that prompts the patient 10 to input the meal size for the selected meal by inputting the number of carbohydrate exchanges the patient 10 is consuming or about to consume. In some examples, the carbohydrate exchange window 810 includes user-selectable links 812, 814, 816, 818, 820 each including a respective image that corresponds to a type of carbohydrate exchange for the patient's meal. The link 812 is associated with a Milk carbohydrate exchange, the link 814 is associated with a Fruit carbohydrate exchange, the link 816 is associated with a Starch carbohydrate exchange, the link 818 is associated with a Vegetable carbohydrate exchange, and the link 820 is associated with a Sweet carbohydrate exchange. Moreover, each user-selectable link 812-820 may include a patient-selectable positive ("+")

button for inputting a carbohydrate exchange each time the patient 10 selects the positive ("+") button and a patient-selectable negative ("−") button for removing a carbohydrate exchange each time the patient 10 selects the negative ("−") button. For instance, the patient 10 may select the positive ("+") button for the link 814 when patient consumes a banana and an apple for the selected meal type (e.g., lunch). The dosing controller 160 may obtain an insulin to carbohydrate ratio from the patient's SubQ information 216a stored within the memory hardware 24, 134, 144 for calculating a recommended meal bolus for the patient 10 in response to the number of carbohydrate exchanges input by the patient 10 via the carbohydrate exchange window 810.

In another implementation, the patient 10 inputs the meal size for the selected meal type by inputting a total number of carbohydrates the patient 10 consumed. FIG. 8B provides a schematic view 800b of an example GUI of the patient management program 200 rendering a carbohydrate input window 850 for the selected meal type (e.g., Lunch) that prompts the patient 10 to input the meal size for the selected meal by inputting the number of carbohydrates the patient 10 is consuming or about to consume. In some examples, the carbohydrate input window 850 provides a carbohydrate input field 852 that enables the patient 10 to input the number of carbohydrates for the selected meal type. In these examples, the example GUI may provide a touch screen keypad for inputting the number carbohydrates or the patient 10 may input the number of carbohydrates to the carbohydrate input field 852 using the keyboard 119 and/or via speech recognition.

The example GUIs of FIGS. 8A and 8B may render the recommended insulin dose window 720 providing the correction bolus graphic 722 and the meal bolus graphic 724, the patient-selectable total dosage button 730 for allowing the patient 10 to view and confirm the recommended total dosage of insulin, and the patient-selectable change dosage button 732 for allowing the patient 10 to change the recommended total dosage of insulin by inputting a new value when the change dosage button 732 is selected.

Figures 9A, 9B:
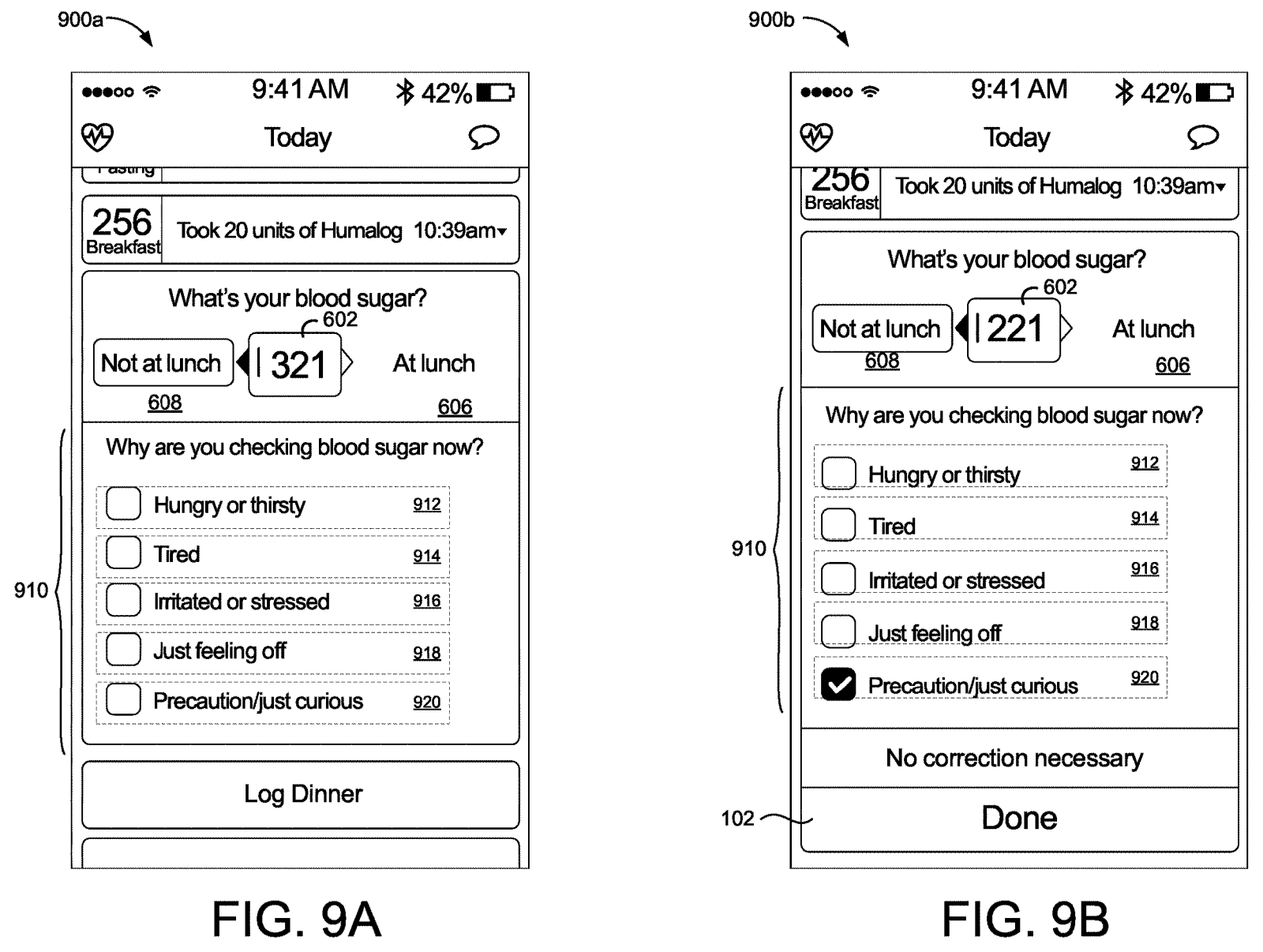

FIGS. 9A and 9B provide schematic views 900a, 900b of example GUIs of the patient management program 200 displayed on the display 116 of the patient device 110 for prompting the patient 10 to input a rational for obtaining the current BG measurement when the patient 10 selects the non-meal button 608 (e.g., user-selectable link 606). As set forth above, the non-meal button 608 indicates that the current BG measurement input to the BG input field 602 is dissociated from the meal type indicated by the patient-selectable meal type button. For instance, FIGS. 9A and 9B show the non-meal button 608 indicating that the current BG measurement equal to 321 mg/dl in the BG input field 602 is dissociated from the Lunch meal type indicated by the selectable meal type button 606. The patient management program 200 may augment an area of the GUI including the non-meal button 608 when the patient selects the non-meal button 608 and prompt the patient to input the rational for obtaining the current BG measurement. For example, the example GUIs of FIGS. 9A and 9B highlight an area around the non-meal button 608 when selected by the patient 10.

FIG. 9A shows the GUI rendering rational window 910 that requests the patient 10 to input the rational for obtaining the current BG measurement that is dissociated from a meal type. In some examples, the rational window 910 includes patient-selectable rational boxes 912, 914, 916, 918, 918, 920 each describing a respective rational/reasoning for obtaining the current BG measurement and enabling the patient 10 to log the rational when the corresponding one of the rational boxes 912-920 is selected by the patient 10. For instance, the patient 10 may tap the rational box 912-920 that most accurately describes the patient's rational for obtaining the current BG measurement. In some examples, the GUI of the patient management program 200 augments the rational box 912-920 selected by the patient 10. FIG. 9B shows the GUI augmenting the rational box 920 selected by the patient 10 indicating that the patient was being precautious and/or curious. The example GUI of FIG. 9B also provides a patient-selectable Done button 930, that when selected by the patient 10, causes the patient device 110 to transmit the selected rational input by the patient 10 to the dosing controller 160 for storage within the memory hardware 24, 134, 144.

Figure 10B:
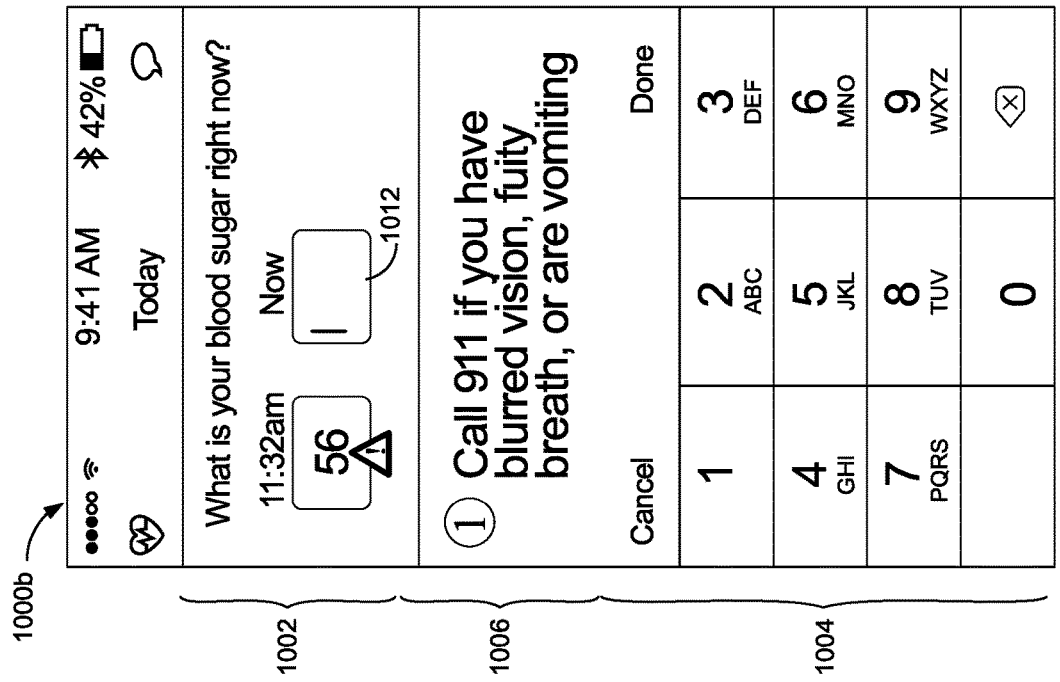
FIGS. 10A-10C are schematic views of example graphical user interfaces displaying a hypoglycemic view when a patient's blood glucose is less than a hypoglycemic blood glucose value.
Figure 10A:
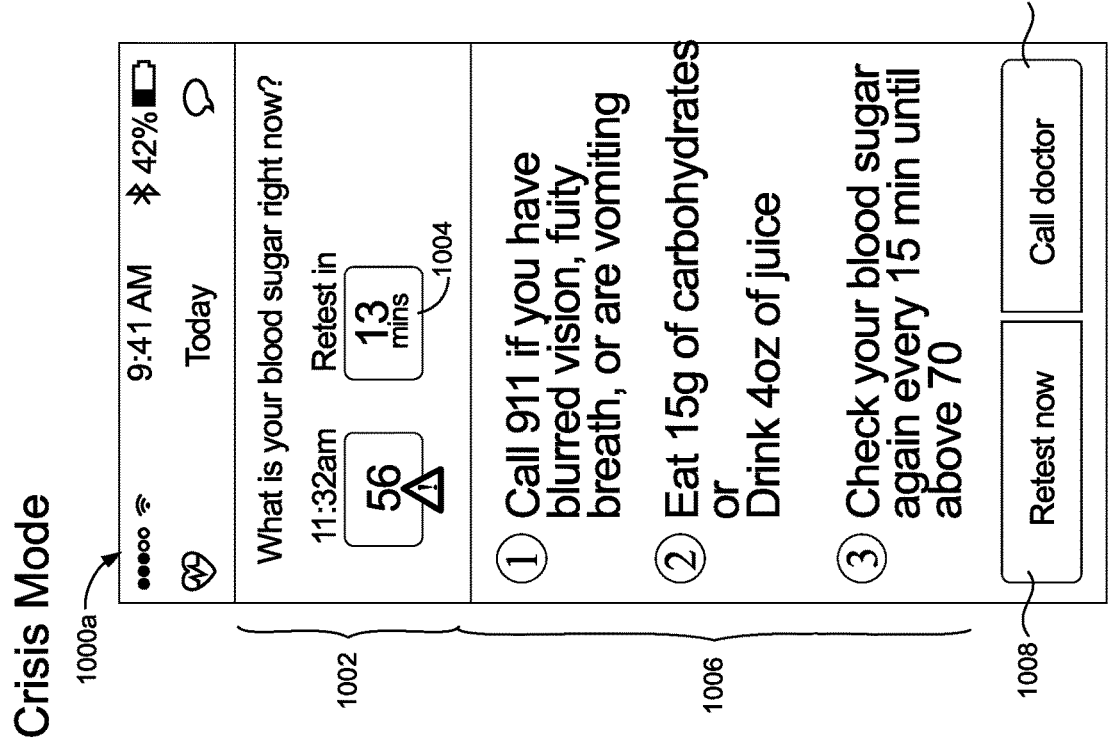
Figure 10C:
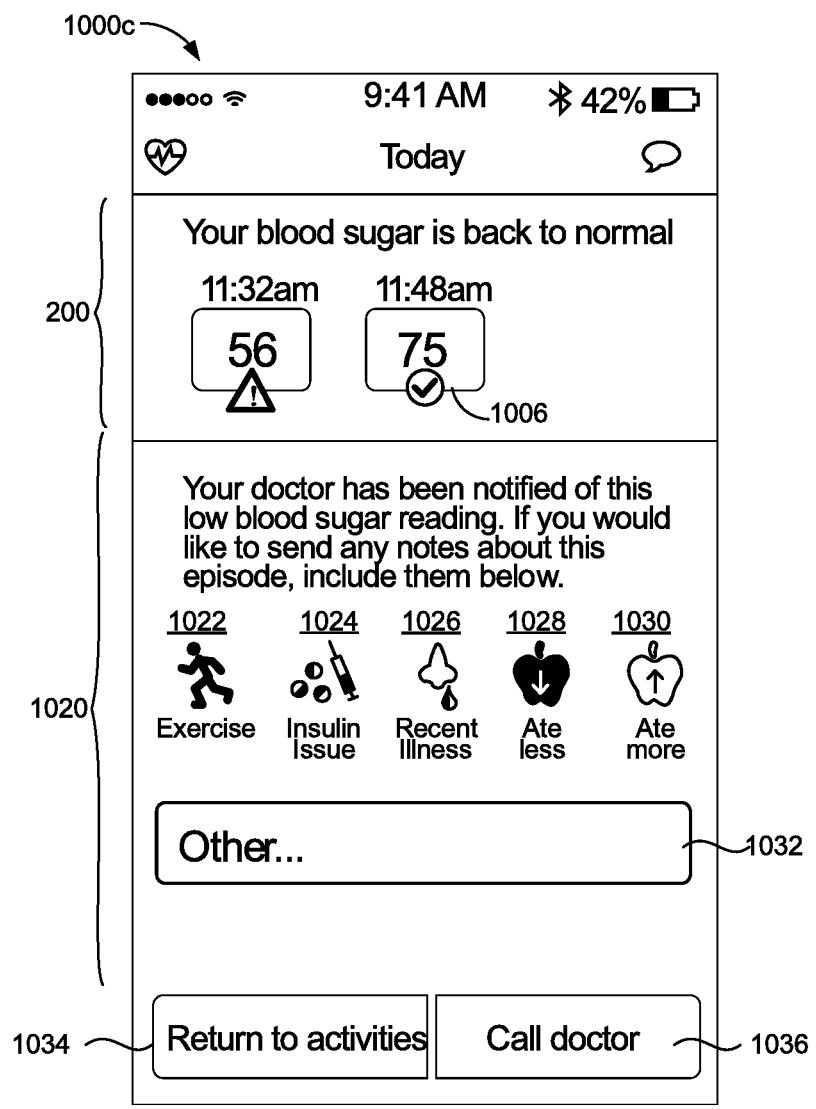

FIGS. 10A-10C show schematic views 1000a-c of example GUIs of the patient management program 200 displayed on the display 116 of the patient device 110 that render a hypoglycemia view. In some implementations, when the current BG measurement input to the BG input field 602 of FIGS. 6A and 6B is less than a hypoglycemia blood glucose value, the dosing controller 160 transmits a low blood glucose alert notification 308 to the patient device 110 that causes the patient management program 200 to render the hypoglycemia view on the patient display 116. The hypoglycemia view may include an alert window 1002 that provides a value of the current BG measurement and the BG time associated with the current BG measurement. The alert window 1002 also provides a countdown timer 1004 indicating a remaining amount of time until the patient 10 is requested to re-test his or her blood glucose using the glucometer 124. The example GUI of FIG. 10A shows the current BG measurement equal to 56 mg/dl and the BG time equal to 11:32 am while the countdown timer 1004 indicates 13 minutes remaining until the patient 10 needs to re-test his or her blood glucose. The countdown timer 1004 initializes at 15 minutes in some examples.

In some examples, the hypoglycemia view displayed by the example GUI of the patient management program 200 displays hypoglycemia patient instructions 1006 for treating the hypoglycemia episode associated with the current BG measurement. For instance, FIG. 10A shows the hypoglycemia patient instructions 1006 stating (1) "Call 911 if you have blurred vision, fruity breath, or are vomiting;" (2) "Eat 15 g of carbohydrates or Drink 4 oz of juice;" and (3) "Check your blood sugar again every 15 mins until above 70."

Additionally, the hypoglycemia view displayed by the example GUI may display patient-selectable Retest now button 1008 and/or a patient-selectable Call doctor button 1010. For example, when the patient selects the Retest now button 1008, the patient management program 200 may prompt the patient 10 to retest his or her blood glucose measurement at the present moment. For instance, FIG. 10B shows the alert window 1002 providing a BG input box 1012 in place of the countdown timer 1004 in response to the patient 10 selecting the Retest now button 1008. In other examples, the patient management program 200 provides the BG input box 1012 in response to the countdown timer 1004 lapsing. In some examples, the patient management program 200 displays a touchscreen keypad 1004 for use by the patient 10 to input a subsequent BG measurement into the BG input box 1012. Alternatively, the patient 10 may input the subsequent BG measurement to the BG input box 1012 using the keyboard 119 and/or via speech recognition techniques. In some implementations, the patient management program 200 causes the patient device 110 to initiate a voice call with the HCP 40 when the patient selects the Call doctor button 1010.

In some examples, the patient management program 200 augments the alert window 1002 of the displayed hypoglycemia view when the subsequent BG measurement input to the BG input box 1006 is greater than the hypoglycemia blood glucose value. For instance, the example GUI of FIG. 10C shows the patient management program 200 providing an exclamation graphic indicating the value of the subsequent BG measurement equal to 76 mg/dl is greater than the hypoglycemia blood glucose value. Here, the alert window 1002 of the displayed hypoglycemia view may also provide a notification informing the patient 10 that the patient's blood glucose back to normal. In some implementations, the patient management program 200 causes the patient device 110 to inform the user device 142 associated with the HCP 40 of the patient's hypoglycemia episode. The patient management program 200 may also prompt the patient 10 to optionally input a cause associated with the hypoglycemia episode by displaying a hypoglycemia cause window 1020 (FIG. 10C) when the subsequent BG measurement input to the BG input box 1006 is greater than the hypoglycemia blood glucose value.

Referring to the example GUI of FIG. 10C, the hypoglycemia cause window 1020 may include one or more patient-selectable links 1022, 1024, 1026, 1028, 1030 each including link data (e.g., text and/or images) associated with a corresponding cause for the recent hypoglycemia episode. Patient-selectable link 1022 indicates the cause of the hypoglycemia episode was due to exercise, patient-selectable link 1024 indicates the cause of the hypoglycemia episode was due to insulin issues, patient-selectable link 1026 indicates the patient 10 the cause of the hypoglycemia episode was due to a recent illness, patient-selectable link 1028 indicates the cause of the hypoglycemia episode was due to the patient 10 consuming less food than indicated by the meal size input, and patient-selectable link 1030 indicates the cause of the hypoglycemia episode was due to the patient 10 consuming more food than indicated by the meal size input. The hypoglycemia cause window 1020 may also render a hypoglycemia cause box 1032 that enables the patient 10 to input a cause of the most recent hypoglycemia episode when none of the patient-selectable link 1022-1030 displayed by the GUI adequately describe the cause of the episode.

Additionally, the hypoglycemia view displayed by the example GUI may display a patient-selectable Return to activities button 1034 and/or the patient-selectable Call doctor button 1010. For example, when the patient selects the Return to activities button 1034, the patient management program 200 may the patient device 110 to exit the hypoglycemia view.

Referring to FIGS. 11A-11E, in some implementations, the user device 142 of the clinic system 140 executes the patient management program configured to display on a screen (e.g., display 146) in communication with the user device 142 a GUI 1100, 1100a-d having the trend window 1102 of BG measurements on a timeline. For instance, the user device 142 may obtain the BG measurements of a patient 10 and BG times associated with the time of measuring each BG measurement from the glucometer 124 associated with the patient 10. Here, the patient 10 refers to one of one or more patients the HCP 40 associated with the user device 142 is treating remotely via communications through the network 20 and in association with the dosing controller 160.

In some examples, the patient management program 200 executing on the user device 142 is configured to receive magnifying inputs from the HCP 40 in the trend window 1102 for a magnification window 1104 superimposed on a segment of the timeline to specify a date range for a magnified window 1106, 1106a-e. Here, the HCP 40 (e.g. user) may apply the magnifying inputs in the trend window 1102 to set a start date and an end date for the specified date range. For instance, a start date graphical point 1105 and an end date graphical point 1107 may be superimposed on the trend window 1102 to define the magnification window 1104 and may be manipulated by the HCP 40 (e.g., touched, or clicked on) to slide the points 1105 and/or 1107, and therefore stretch or shorten the magnification window 1104, to set the specified date range. The examples of FIGS. 11A-11E show the magnification window 1104 defining a start date of "18Feb" and an end date of "Today" for the magnified window 1106. Once the date range for the magnified window 1106 is set, the patient management program 200 is configured to display the magnified window 1106 in the GUI 1100. In some implementations, the magnified window includes the BG measurements of the patient 10 from the specified date range. Moreover, the GUI 1100 of the patient management program 200 may also display one or more information windows 1108a-d each including respective quantitative information associated with the BG measurements from the specified date range.

In some implementations, the quantitative information of each information window 1108a-d may be displayed in the GUI 1100 in the form of a user-selectable link each including link data, i.e., text and/or an image that describes the corresponding quantitative information associated with the BG measurements from the specified date range. In the examples of FIGS. 11A-11E, each of the information windows 1108a-d are associated with data, such that when the HCP 40 selects the window 1108a-d, the patient management program 200 displays the corresponding quantitative information in the magnified window 1106. The example GUIs 1100 show a first information window 1108a including quantitative information related to a number of BG measurements (e.g., BG readings) of the patient 10 per day for the specified date range, a second information window 1108b including quantitative information related to an average daily BG measurement for the specified date range, a third information window 1108c including quantitative information related to an average A1c value for the specified date range, and a fourth information window 1108d including quantitative information related to insulin dosing information for the specified date range. Here, the insulin dosing information may include an average total daily dosage of insulin, insulin adherence, and/or average doses of insulin injected by the patient during each of the patient's scheduled BG time intervals.

Figure 11A:
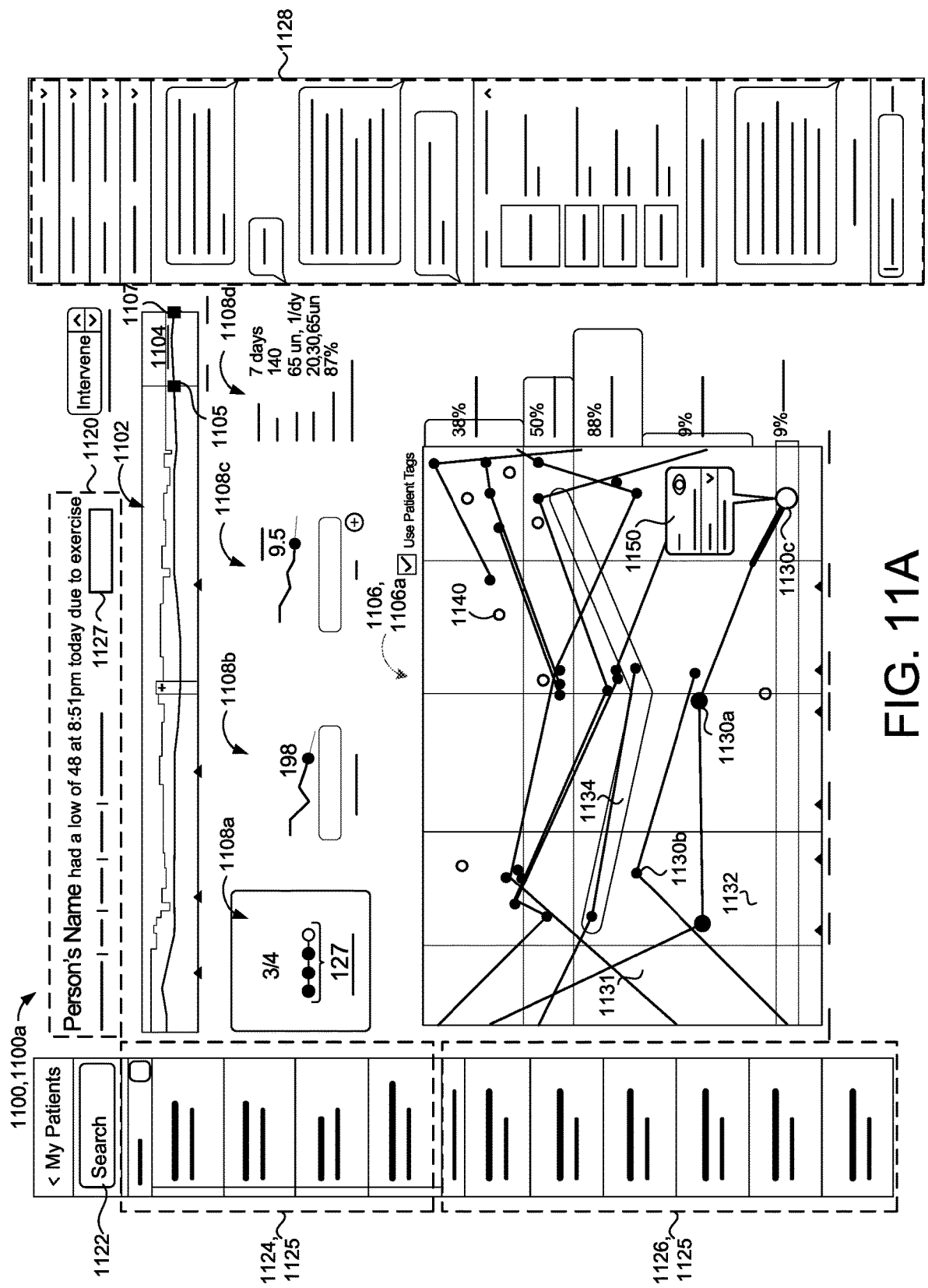
FIGS. 11A-11D are schematic views of example graphical user interfaces displaying a timeline of blood glucose measurements for a patient.

Referring to FIG. 11A, the example GUI 1100a of the patient management program 200 displays patient information 1120 for the patient 10 associated with the displayed trend window 1102 of BG measurements. For instance the patient information 1120 includes information such as the patient's name, age, height, weight, and contact information. The patient information 1120 may also indicate any alerts associated with the patient, such as recent hypoglycemic episodes and a cause for the hypoglycemic episode. For instance, the patient management program 200 may render an alert graphic 1127 in the patient information 1120 indicating the recent hypoglycemic episode in response to the patient 10 selecting one of the patient-selectable links 1022, 1024, 1026, 1028, 1030 in the hypoglycemia cause window 1020 displayed on the patient's display 116 of FIG. 10C.

The patient management program 200 may also allow the HCP 40 to search for other patients the HCP 40 treats by entering a name in a name search box 1122. Moreover, the patient management program 200 may display an alert list 1124 of patients under the supervision of the HCP 40 that have recent alert conditions. For instance, the alert list 1124 may provide a list of patient names, a type of alert condition, and a time of the alert condition. The alert list 1124 may augment alerts that have been resolved by rendering a graphic in an area near the resolved patient's name. Additionally, the patient management program 200 may superimpose an alert graphic 1127 in the GUI 1100a proximate to the patient associated with the alert condition. The alert graphic 1127 may include a value of the most recent blood glucose measurement associated with the alert condition. The alerts may include, but are not limited to, hypoglycemic episodes, hyperglycemic episodes, and no BG measurements received. The alert list 1124 allows the HCP 40 to efficiently review patient's requiring attention by prioritizing the patient's in the alert list 1124 by severity. Additionally or alternatively, the patient management program 200 may display an update list 1126 of patients requiring treatment updates (e.g., new recommended insulin dosing regimens). The patient management program 200 is configured to display the trend window 1102 of BG measurements for different patients by selecting the patients from either of the lists 1124 or 1126 or patients entered in the name search box 1122. The alert list 1124 and the update list 1126 may collectively provide a monitoring window 1125 of patients 10 under the supervision of the HCP 40 that may require attention due to an alert condition or in need of a new recommended insulin dosing regimen soon.

In some implementations, the patient management program 200 is further configured to display a communication window 1128 in the GUI 1100a. Here, the communication window 1128 may show a history of communications (e.g., text messages, emails, video conferences, phone calls, etc.) between the HCP 40 and the patient 10. The communication window 1128 may be substantially similar to the example GUI displayed on the patient device 110 of FIG. 5B.

With continued reference to FIG. 11A, the BG measurements of the magnified window 1106a include interactive points 1140 and 1130, 1130a-c within associated ones of scheduled blood glucose time intervals based on the blood glucose times. Here, the blood glucose time intervals may correspond to fasting, pre-breakfast, pre-lunch, pre-dinner, and bedtime. More particularly, the patient management program 200 renders the interactive points 1130, 1140 in the magnified window 1106a in response to the patient 10 selecting the first information window 1108a including quantitative information related to the number of BG measurements (e.g., BG readings) of the patient 10 per day for the specified date range. The patient management program 200 may highlight, or otherwise augment, an area of the GUI 1100a around the first information window 1108a to indicate that the magnified window 1106a is associated with the HCP's selection of the first information window 1108a. The interactive points 1140 are "unfilled" and correspond to BG measurements the dosing controller 160 will not use for calculating the next recommended insulin dosing regimen for the patient. On the other hand, the interactive points 1130 are "filled" and correspond to BG measurements the dosing controller 160 will use for calculating the next recommended insulin dosing regimen for the patient 10.

In response to receiving the magnifying inputs for the magnification window 1104, the patient management program 200 may determine a representative average BG value for each of the scheduled BG time intervals and superimpose an average BG graphic 1134 on the magnified window 1106a based on the representative average blood glucose values for the scheduled BG time intervals. The average BG graphic 1134 in the example of FIG. 11A reveals that the patient's average BG measurements are higher during the bedtime BG time interval than during the lunch and breakfast BG time intervals.

In some implementations, the patient management program superimposes a first line 1131 on the magnified window 1106a representing an upper BG limit (e.g. 180 mg/dl) of the target BG range and a second line 1132 on the magnified window 1106a representing a lower BG limit (e.g., 70 mg/dl) of the target BG range. In some examples, the upper and lower BG limits of the target BG range are obtained from the patient SubQ information 216a stored in the memory hardware 24, 134, 144. In some scenarios, the interactive points 1130a associated with the BG measurements within the target BG range display as a first representation, the interactive points 1130b associated with the BG measurements greater than the upper BG limit (e.g., first line 1131) display as a second representation, and the interactive points 1130c associated with the BG measurements less than the lower BG limit (e.g., second line 1132) display as a third representation or the second representation.

In some examples, the patient management program 200 aggregates the BG measurements greater than the upper BG limit (e.g., first line 1131) into a first hyperglycemia range, a second hyperglycemia range, and a third hyperglycemia range. The first hyperglycemia range may include BG measurements greater than 180 mg/dl and less than or equal to 250 mg/dl, the second hyperglycemia range may include BG measurements greater than 250 mg/dl and less than 300 mg/dl, and the third hyperglycemia range may include BG measurements greater than 300 mg/dl. Moreover, the patient management program 200 may assign a percentage of distribution based on the number of BG measurements less than the lower BG limit (e.g., second line 1132), the number of BG measurements within the BG target range (e.g., between the first and second lines 1131 and 1132), and the number of BG measurements within each of the first hyperglycemia range, the second hyperglycemia range, and the first hyperglycemia range. The example of FIG. 11A shows that 3% of the BG measurements are less than the lower BG limit, 9% of the BG measurements are within the BG target range, 88% of the BG measurements are within the first hyperglycemia range, 50% of the BG measurements are within the second hyperglycemia range, and 38% of the BG measurements are within the third hyperglycemia range.

In some implementations, the interactive points 1130, 1140 associated with the BG measurements are patient-selectable such that, in response to the HCP 40 selecting (e.g., touching, hovering a cursor over, or clicking on) one of the interactive points 1130, 1140 on the magnified window 1106a, the patient management program 200 may obtain quantitative information related to the BG measurement associated with the selected interactive point 1130, 1140. In these implementations, the patient management program 200 may illuminate the selected interactive point 1130, 1140, query the memory hardware 24, 134, 144 to obtain the quantitative information related to the BG measurement, and display a pop-up window 1150 including the obtained quantitative information for the HCP 40 to view.

For instance, the HCP 40 may be curious about one of the patient's BG measurements that is below the lower BG limit, and may select (e.g., touch, hover, or click on) the corresponding interactive point 1130c to prompt the patient management program to obtain the quantitative information for display in the pop-up window 1150. FIG. 11A shows the pop-up window 1150 indicating that the patient's BG value was equal to 48 mg/dl on February 22 at 8:52 pm after the patient consumed dinner. The quantitative information in the pop-up window 1150 may include other information such as, but not limited to, a dosage of insulin administered by the patient before obtaining the BG measurement, a meal size of the meal occurring before the BG measurement, and/or whether the patient 10 was exercising.

Figure 11B:
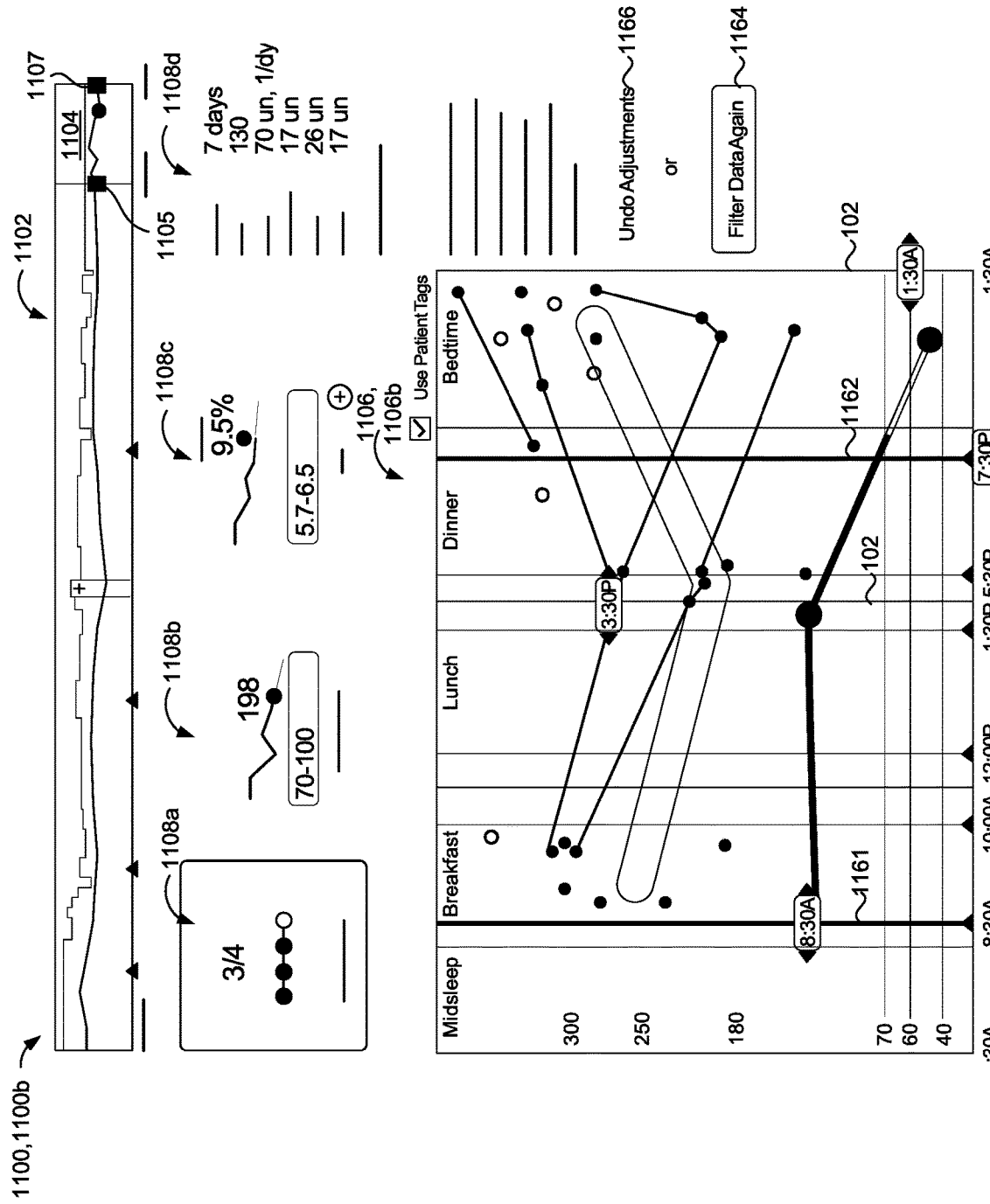

Referring to FIG. 11B, in some implementations, the patient management program 200 is configured to receive filtering inputs in the magnified window 1106b from the HCP 40 to define a specified time range for the magnified window 1106b. In some examples, the program 200 receives the filter inputs when the HCP 40 manipulates a first interactive cursor 1161 superimposed on the magnified window to set a lower time limit for the specified time range. Additionally or alternatively, the program 200 receives the filter inputs when the HCP 40 manipulates a second interactive cursor 1162 superimposed on the magnified window to set an upper time limit for the specified time range. For instance, the first interactive cursor 1161 in the example of FIG. 11B indicates the lower time limit equal to 8:30 am while the second interactive cursor 1162 indicates the upper time limit equal to 7:30 pm. The patient management program 200 may prompt the HCP 40 to confirm a new specified time range for the magnified window 1106b by selecting a Filter Data Again button 1164 that causes the patient management program 200 to filter the BG measurements that fall within the specified time range for the magnified window 1106b. Here, the patient management program 200 queries the memory hardware 24, 134, 144 to obtain quantitative information related to the BG measurements within the specified time range of the magnified window and displays an information window including the quantitative information related to the BG measurements within the specified time range of the magnified window 1106b. Conversely, the program 200 may allow the HCP 40 to cancel the new specified time range by selecting an Undo Adjustments button 1166 so that no filtering is performed. In some examples, the interactive points 1130 associated with the BG measurements within the specified time range (e.g., between cursors 1161 and 1162) display as a representation that is different than a representation for the BG measurements outside the specified time range (e.g., occurring before the lower time limit or occurring after the upper time limit).

Figure 11C:
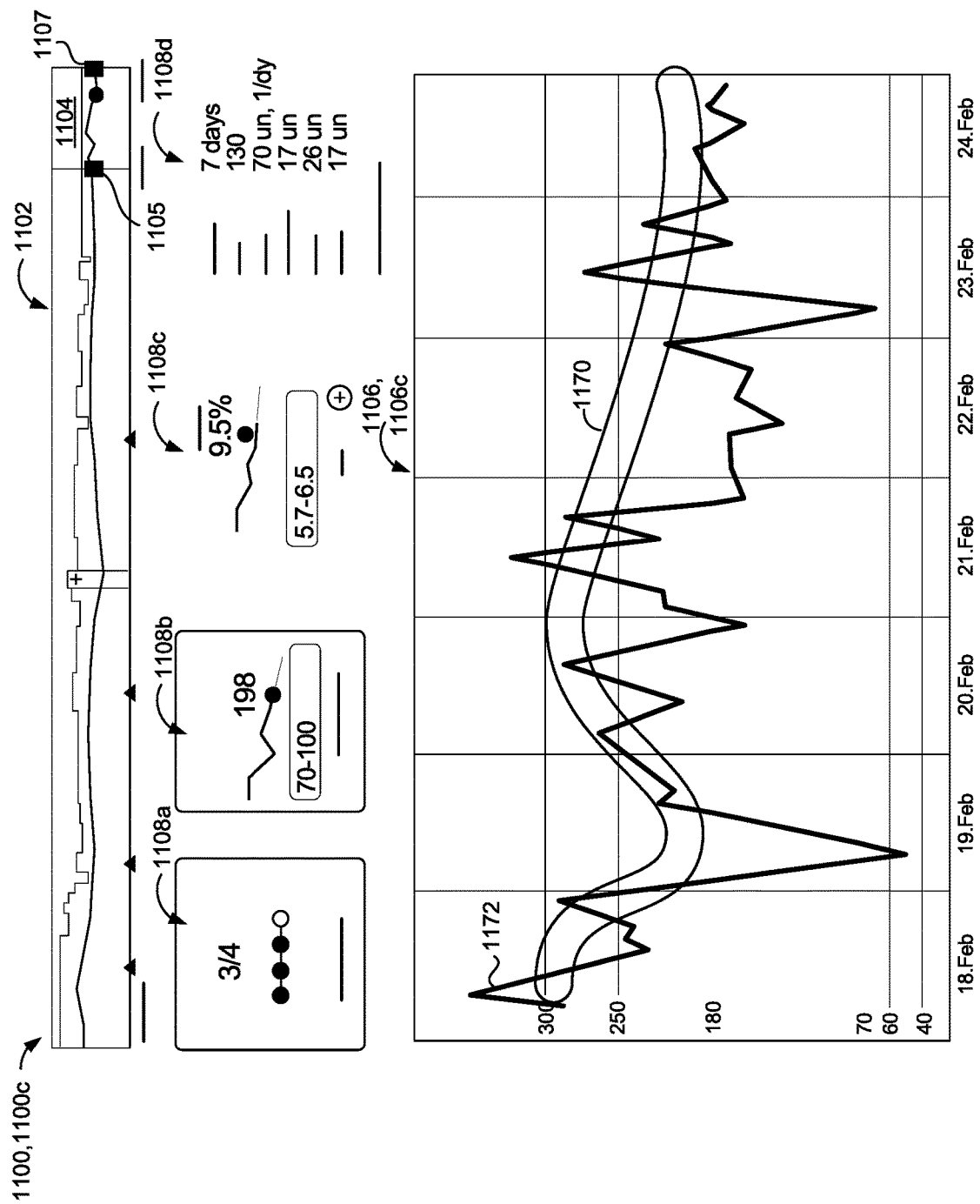

In some implementations, in response to receiving the magnifying inputs 1105, 1107 for the magnification window 1104 superimposed on the segment of the timeline 1102 to specify the date range for the magnified window 1106, the patient management program 200 determines a daily average BG value for each date of the specified date range. For example, the second information window 1108b may be associated with the daily average BG value for each date of the specified date range. The example GUI 1100c of FIG. 11C shows the patient management program 200 superimposing an average BG graphic 1170 on the magnified window 1106c based on the daily average blood glucose values for the specified date range. The patient management program 200 may superimpose the average BG graphic on the magnified window 1106c response to the patient selecting the second information window 1108b. In some examples, the patient management program 200 displays a blood glucose plot 1172 on the magnified window 1106c for each BG measurement from the specified date range. Here, the plot extends through each date of the specified date range based on each BG measurement value and corresponding BG time.

Figure 11D:
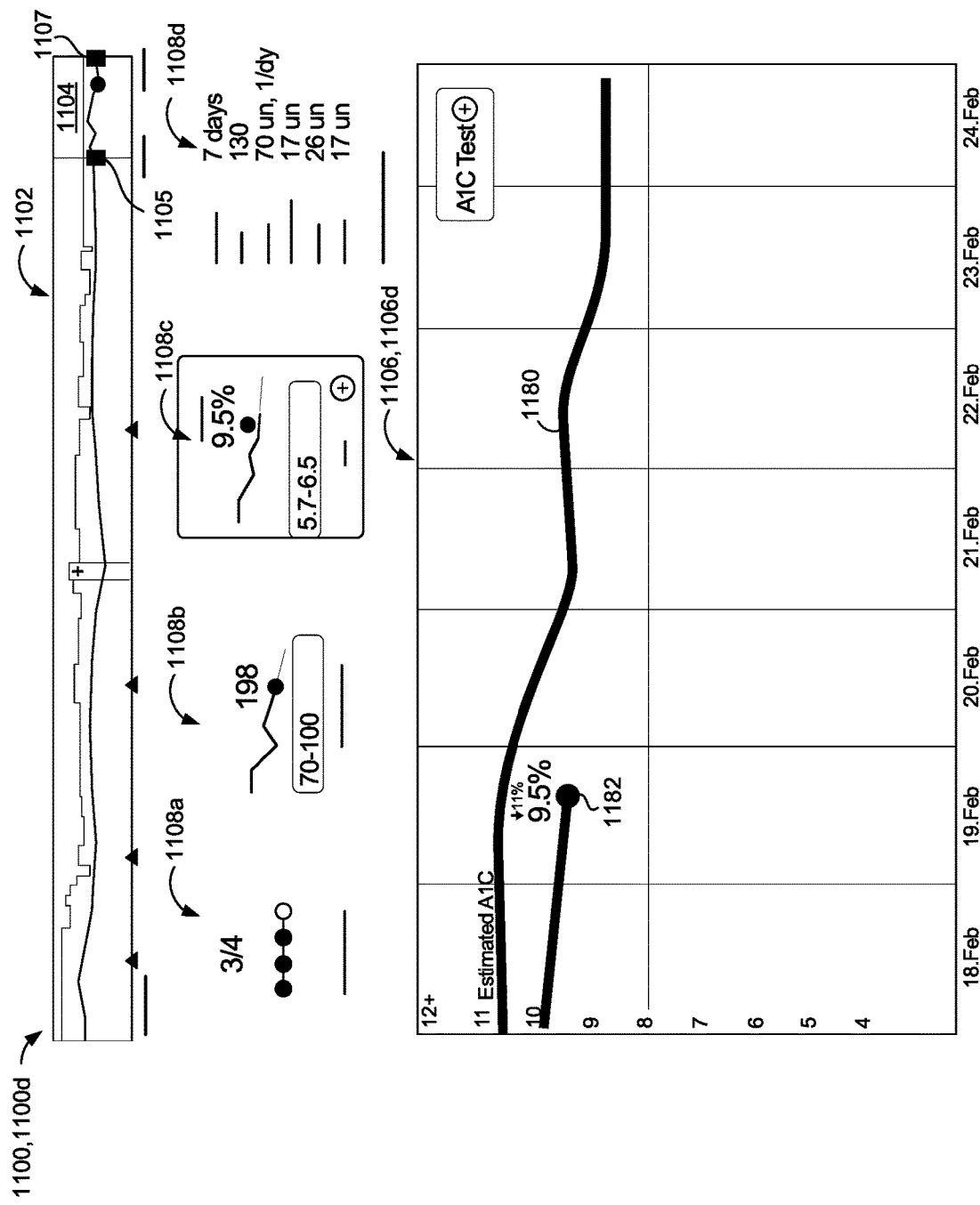

Referring to FIG. 11D, the patient management program 200 may determine an estimated hemoglobin A1c value for each date of the specified date range and superimpose an average hemoglobin A1c graphic 1180 on the magnified window 1106d based on the estimated hemoglobin A1c values of the specified date range. The patient management program 200 may also superimpose a point 1182 corresponding to an actual hemoglobin A1c value for the patient 10 on the magnified window 1106d.

Figure 11E:
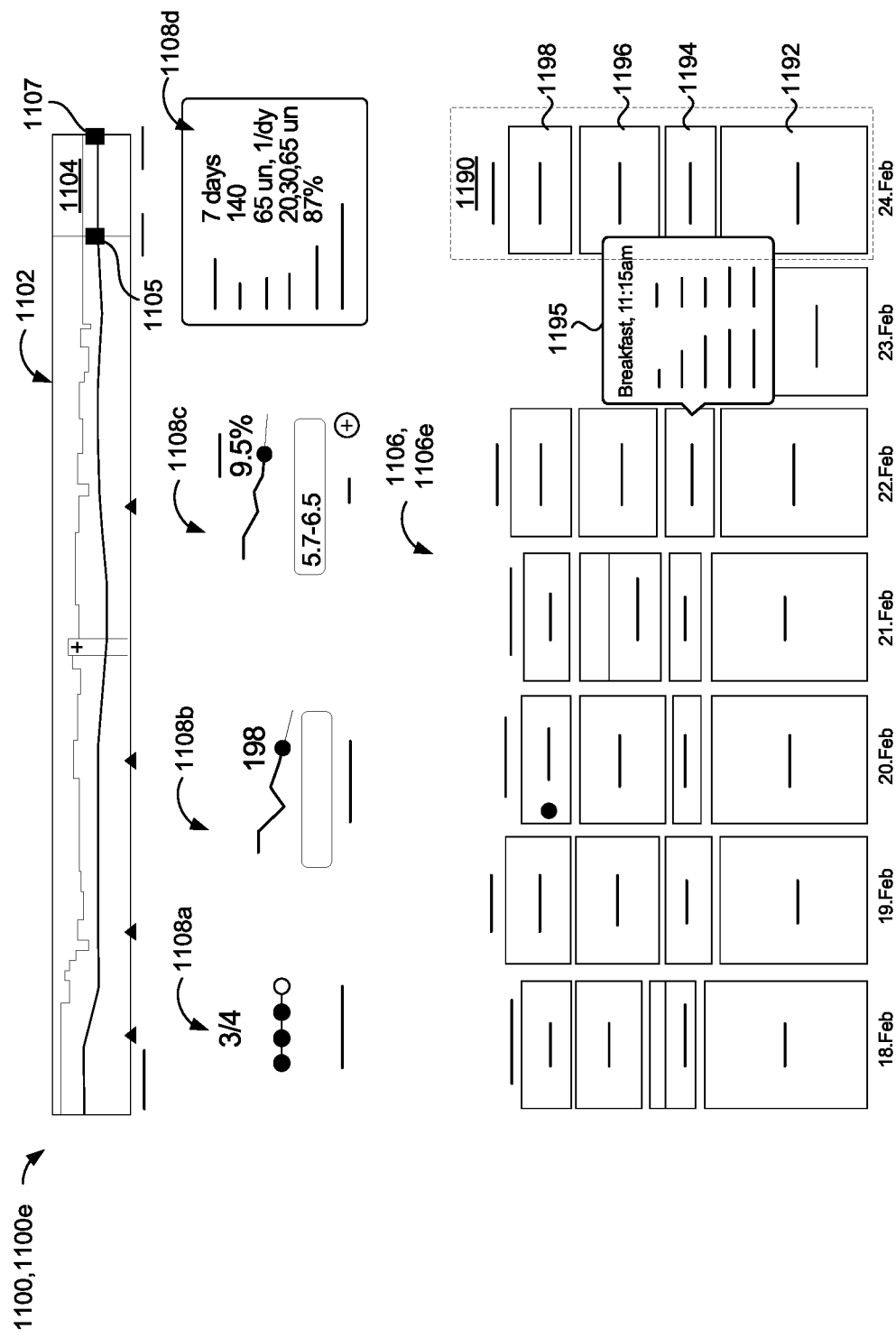

Referring to FIG. 11E, in some implementations, the patient management program 200 is configured to query the memory hardware 24, 134, 144 to obtain doses of insulin administered by the patient 10 for each date of the specified date range and superimpose a plot 1190 of doses of insulin administered by the patient 10 for each date of the specified date range on the magnified window 1106e. The plot 1190 may include a total daily dose (TDD) of insulin for each date based on the number of units of insulin administered by the patient throughout the day during scheduled intervals. For instance, patient management program 200 may display dosage graphics 1192, 1194, 1196, 1198 indicating the number of units of insulin administered by the patient 10 during respective ones of basal dose, breakfast bolus dose, lunch bolus dose, and dinner bolus dose. In some implementations, each dosage graphic 1192, 1194, 1196, 1198 is interactive such that, in response to the HCP 40 selecting e.g., touching, hovering a cursor over, or clicking on) one of the graphics 1192, 1194, 1196, 1198 on the magnified window 1106e, the patient management program 200 displays a pop-up window 1195 including detailed information related to the dosage of insulin associated with the selected dosage graphic 1192, 1194, 1196, 1198. For example, FIG. 11E shows the pop-up window 1195 providing information related to the patient's breakfast bolus such as the BG measurement, the number of carbohydrates consumed, the meal bolus, the correction bolus, and the insulin to carbohydrate ratio for the patient.

Referring to FIG. 12A, in some implementations, the user device 142 of the clinic system 140 executes the patient management program configured to display a patient dashboard GUI 1200 having a list 1202 of patients 10 under the supervision of the HCP 40. The patient list 1202 may provide patient information for each patient 10 such as name, date of birth (DOB), clinic, A1C value, average BG measurement value, TDD, when a next update is due (e.g., Update), and any pending alert conditions (e.g., Alert). The patient management program 200 may display the patient information as data including text and/or images. For example, image plots for the patients' A1C and average BG measurement values may be displayed to reveal a trend for the corresponding data. The alert conditions may include hypoglycemia events such as when a patient had a recent blood glucose measurement that was less than a hypoglycemia blood glucose value, hyperglycemia events such as when a patient had a recent blood glucose measurement that was greater than a hyperglycemia blood glucose measurement, and no BG data conditions such as when a patient 10 has failed to log BG measurements during scheduled time intervals.

Figure 12:
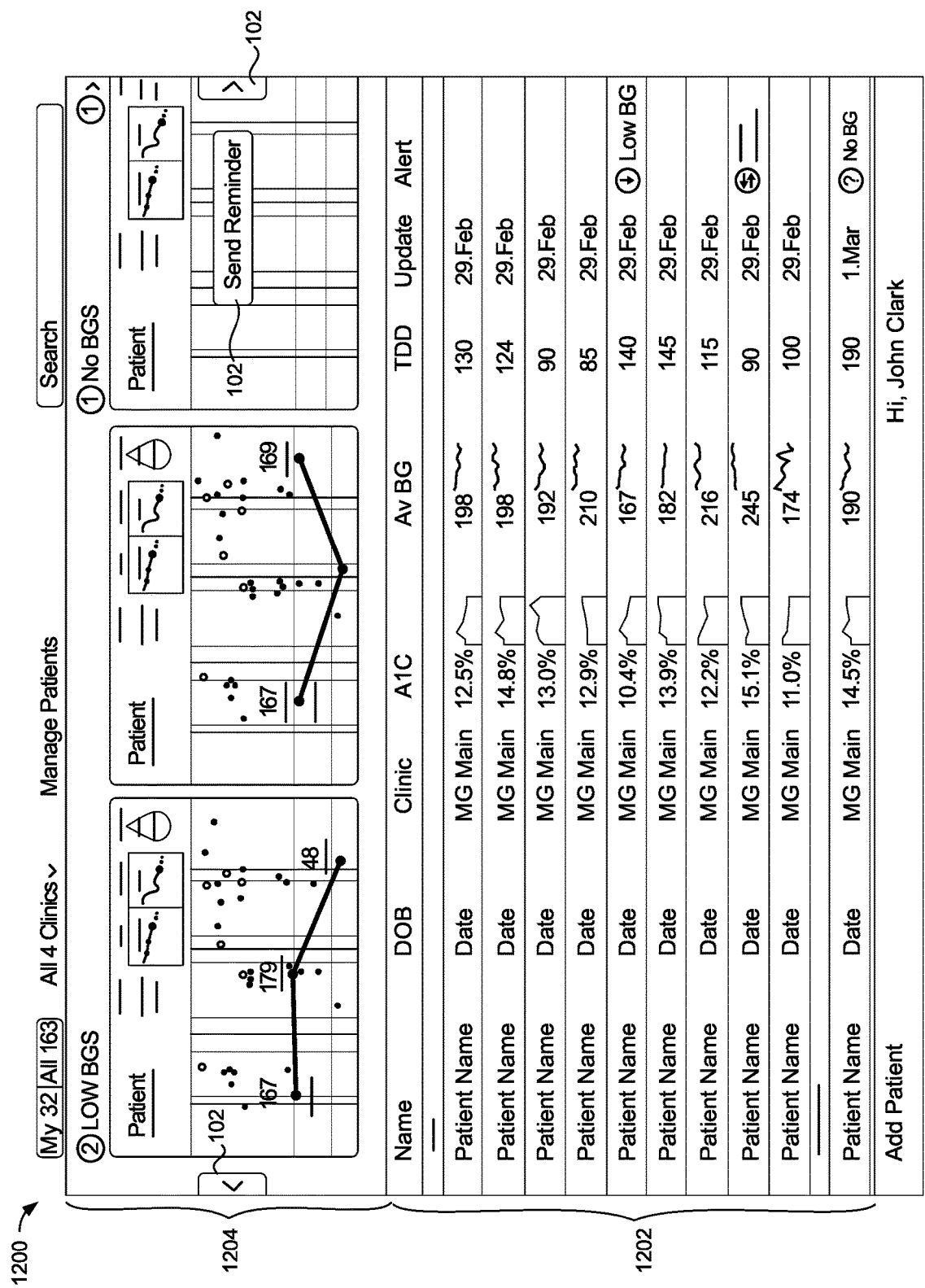
FIG. 12 is a schematic view of an example graphical user interface displaying a dashboard of a list of patients under the supervision of a healthcare professional.

In some examples, the patient dashboard GUI 1200 of FIG. 12 also displays patient profile cards 1204, 1204a-c for each patient 10 flagged as having a recent alert condition and therefore requiring review by the HCP 40. The patient profile cards 1204 may be displayed horizontally and include pertinent patient information such as name, contact information, when next update is due, average A1c value, average BG value and the corresponding alert condition. The patient profile cards may be sorted and arranged a together based on the alert condition. FIG. 12 shows patient profile cards 1204a and 1204b each associated with a patient who had a hypoglycemic event (e.g., "Low BGs") while patient profile card 1204c is associated with a patient who has not reported any BG data. The patient management program 200 may display a Send Reminder button 1220 in the patient profile card 1204c associated with the patient who has not reported any BG data. In some examples, the patient management program 200 causes the user device 142 to transmit the blood glucose request notification 308 (FIG. 3B) to a user device 110 associated with the patient 10 who has not reported any BG data when the HCP 40 selects the Send Reminder button 1220.

Navigation buttons 1206 and 1208 may allow the HCP 40 to scroll horizontally to view any patient profile cards 1204 not currently displayed. Moreover, a name search filed 1210 may allow the HCP 40 to input a name of a patient 10 under the supervision of the HCP 40. The patient management system 200 may allow the HCP 40 to filter patients by clinic or by a specific clinician.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs software, software applications or code) include machine instructions for a programmable processor and can be implemented in a high-level procedural and/or object-oriented programming language, so and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not so necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile a feedback; and input from the user can be received in any form, including acoustic, speech, or tactile input. In addition, a computer can interact with a user by sending documents to and receiving documents from a device that is used by the user, for example, by sending web pages to a web browser on a use's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be so construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method comprising:
    obtaining, at data processing hardware, blood glucose measurements of a patient and blood glucose times associated with a time of measuring each blood glucose measurement from a blood glucose meter associated with the patient; and
    executing, at the data processing hardware, a patient management program configured to display on a screen in communication with the data processing hardware a graphical user interface having a trend window of the blood glucose measurements on a timeline, wherein the patient management program is configured to:
        receive, in the trend window, magnifying inputs from a medical professional for a magnification window superimposed on a segment of the timeline to specify a date range for a magnified window;
        display, in the graphical user interface, the magnified window including the blood glucose measurements of the patient from the specified date range, the blood glucose measurements of the magnified window comprising interactive points within associated ones of scheduled blood glucose time intervals based on the blood glucose times;
        determine, based on the obtained blood glucose measurements and the blood glucose times associated with the time of measuring each blood glucose measurement from the blood glucose meter, an average number of times blood glucose measurements of the patient that were obtained from the blood glucose meter per day within the specified date range; and
        display, in the graphical user interface, a first information window including quantitative information associated with the average number of times blood glucose measurements of the patient that were obtained from the blood glucose meter per day within the specified date range.

2. The method of claim 1, wherein the patient management program is configured to:
    superimpose, in the graphical user interface, a first line on the magnified window representing an upper blood glucose limit of a target blood glucose range; and
    superimpose, in the graphical user interface, a second line on the magnified window representing a lower blood glucose limit of the target blood glucose range.

3. The method of claim 2, wherein the interactive points associated with the blood glucose measurements within the target blood glucose range display as a first representation, the interactive points associated with the blood glucose measurements greater than the upper blood glucose limit display as a second representation, and the interactive points associated with the blood glucose measurements less than the lower blood glucose limit display as a third representation or the second representation.

4. The method of claim 1, wherein the patient management program is configured to, in response to receiving the magnifying inputs:
  determine a representative average blood glucose value for each of the scheduled blood glucose time intervals; and
  superimpose, in the graphical user interface, an average blood glucose graphic on the magnified window based on the representative average blood glucose values for the scheduled blood glucose time intervals.

5. The method of claim 1, wherein the patient management program is configured to:
  receive, in the magnified window, filtering inputs from the medical professional to define a specified time range for the magnified window;
  queries memory hardware in communication with the data processing hardware to obtain quantitative information related to the blood glucose measurements within the specified time range of the magnified window; and
  display, in the graphical user interface, a second information window including the quantitative information related to the blood glucose measurements within the specified time range of the magnified window.

6. The method of claim 5, wherein the interactive points associated with the blood glucose measurements within the specified time range of the magnified window display as a first representation and the blood glucose measurements outside the specified time range of the magnified window display as a second representation different from the first representation.

7. The method of claim 5, wherein the patient management program receives the filtering inputs from the medical professional when the medical professional manipulates a first interactive cursor superimposed on the magnified window to set a lower time limit for the specified time range of the magnified window and/or manipulates a second graphical cursor superimposed on the magnified window to set an upper time limit for the specified time range of the magnified window.

8. The method of claim 1, wherein the patient management program is configured to, in response to the medical professional selecting one of the interactive points on the magnified window:
  illuminate the selected interactive point of the magnified window;
  query memory hardware in communication with the data processing hardware to obtain quantitative information related to the blood glucose measurement associated with the selected interactive point; and
  display a pop-up window including the quantitative information related to the blood glucose measurement associated with the selected interactive point.

9. The method of claim 5, wherein the quantitative information included in the second information window includes at least one of an average blood glucose value, an aggregated blood glucose value for each of the scheduled blood glucose time intervals, a hemoglobin A1c value, an average total daily dose of insulin, or average doses of insulin injected by the patient during each of the scheduled blood glucose time intervals.

10. The method of claim 1, wherein obtaining the blood glucose measurements of the patient comprises receiving, at the data processing hardware, the blood glucose measurements of the patient and the blood glucose times from a patient device in communication with the data processing hardware and the blood glucose meter.

11. A method comprising:
  obtaining, at data processing hardware, blood glucose measurements of a patient and blood glucose times associated with a time of measuring each blood glucose measurement from a blood glucose meter associated with the patient; and
  executing, at the data processing hardware, a patient management program configured to display on a screen in communication with the data processing hardware a graphical user interface having a trend window of the blood glucose measurements on a timeline, wherein the patient management program is configured to:
    receive, in the trend window, magnifying inputs from a medical professional for a magnification window superimposed on a segment of the timeline to specify a date range for a magnified window;
    display, in the graphical user interface, the magnified window including the blood glucose measurements of the patient from the specified date range, the blood glucose measurements of the magnified window comprising a blood glucose plot extending through each date of the specified date range;
    determine, based on the obtained blood glucose measurements and the blood glucose times associated with the time of measuring each blood glucose measurement from the blood glucose meter, an average number of times blood glucose measurements of the patient that were obtained from the blood glucose meter per day within the specified date range; and
    display, in the graphical user interface, a first information window including quantitative information associated with the average number of times blood glucose measurements of the patient that were obtained from the blood glucose meter per day within the specified date range.

12. The method of claim 11, wherein the patient management program is configured to, in response to receiving the magnifying inputs:
  determine an estimated hemoglobin A1c value for each date of the specified date range; and
  superimpose, in the graphical user interface, an average hemoglobin A1c graphic on the magnified window based on the estimated hemoglobin A1c values of the specified date range.

13. The method of claim 11, wherein the patient management program is configured to, in response to receiving the magnifying inputs:
  determine a daily average blood glucose value for each date of the specified date range; and
  superimpose, in the graphical user interface, an average blood glucose graphic on the magnified window based on the daily average blood glucose values for the specified date range.

14. The method of claim 11, wherein the patient management program is configured to, in response to receiving the magnifying inputs:
  query memory hardware in communication with the data processing hardware to obtain doses of insulin administered by the patient for each date of the specified date range; and
  superimpose, in the graphical user interface, a plot of the doses of insulin administered by the patient for each date of the specified date range on the magnified window.

15. The method of claim 11, wherein the patient management program is configured to display, in the graphical user interface, a communication window including a history of communications with the patient.

16. The method of claim 11, wherein the patient management program is configured to display, in the graphical user interface, a monitoring window including a list of patients under the supervision of the medical professional.

17. The method of claim 16, wherein the patient management program is configured to:
   determine an alert condition for one of the patients when a most recent blood glucose measurement of the patient is less than a hypoglycemia blood glucose threshold or greater than a hyperglycemia blood glucose threshold; and
   superimpose, in the graphical user interface, an alert graphic on the monitoring window proximate to the patient associated with the alert condition, the alert graphic comprising a value of the most recent blood glucose measurement associated with the alert condition.

* * * * *